United States Patent
Jacotot et al.

(10) Patent No.: US 11,407,741 B2
(45) Date of Patent: Aug. 9, 2022

(54) COMPOUNDS AND THEIR USE AS SELECTIVE INHIBITORS OF CASPASE-2

(71) Applicants: UNIVERSITÉ DE PARIS, Paris (FR); INSTITUT NATIONAL DE LA SANTE ET DE LA RECHERCHE MEDICALE, Paris (FR); SORBONNE UNIVERSITE, Paris (FR); CENTRE NATIONAL DE LA RECHERCHE SCIENTIFIQUE, Paris (FR)

(72) Inventors: Etienne Jacotot, Paris (FR); Elodie Bosc, Brétigny sur Orge (FR)

(73) Assignees: UNIVERSITE DE PARIS, Paris (FR); INSTITUT NATIONAL DE LA SANTE ET DE LA RECHERCHE MEDICALE, Paris (FR); SORBONNE UNIVERSITE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/650,629

(22) PCT Filed: Sep. 26, 2018

(86) PCT No.: PCT/EP2018/076178
§ 371 (c)(1),
(2) Date: Mar. 25, 2020

(87) PCT Pub. No.: WO2019/068538
PCT Pub. Date: Apr. 11, 2019

(65) Prior Publication Data
US 2020/0317647 A1    Oct. 8, 2020

(30) Foreign Application Priority Data
Sep. 26, 2017   (EP) .................................. 17306270

(51) Int. Cl.
C07D 405/12   (2006.01)
C07D 207/16   (2006.01)
C07D 401/12   (2006.01)
C07D 417/14   (2006.01)

(52) U.S. Cl.
CPC ......... *C07D 405/12* (2013.01); *C07D 207/16* (2013.01); *C07D 401/12* (2013.01); *C07D 417/14* (2013.01)

(58) Field of Classification Search
CPC .. C07D 405/12; C07D 401/12; C07D 207/16; C07D 417/14
See application file for complete search history.

(56) References Cited
U.S. PATENT DOCUMENTS
2012/0196892 A1   8/2012   Chauvier
2019/0351003 A1   11/2019  Karin et al.

FOREIGN PATENT DOCUMENTS
WO   2005/105829 A2   11/2005
WO   2006/056487 A2    6/2006
WO   2009/001322 A2   12/2008
WO   2012/104224 A1    8/2012
WO      2018148250      8/2018

OTHER PUBLICATIONS

Ikemi, J Chem Sci, 2010, vol. 1, 68-71. (Year: 2010).*
Vigneswara, Cells, 2020, vol. 9(1259), 1-45. (Year: 2020).*
Machado, Cell Death and Disease, 2016, vol. 7, e2096, 1-12. (Year: 2016).*
Ahmed, Cell Death and Disease, 2011, vol. 2, e173, 1-10. (Year: 2011).*
International Search Report for corresponding International Application No. PCT/EP2018/076178 dated Oct. 25, 2018.
Written Opinion for corresponding International Application No. PCT/EP2018/076178 dated Oct. 25, 2018.
Michel C. Maillard et al., "Exploiting differences in caspase-2 and -3 S subsites for selectivity: Structure-based design, solid-phase synthesis and in vitro activity of novel substrate-based caspase-2 inhibitors", Bioorganic & Medicinal Chemistry, Pergamon, GB, vol. 19, No. 19, Aug. 9, 2011, pp. 5833-5851, XP028294124.
Marcin Poreba et al., "Small Molecule Active Site Directed Tools for Studying Human Caspases", Chemical Reviews, American Chemical Society, U.S., vol. 115, No. 22, Nov. 25, 2015, pp. 12546-12629, Xp002758422.
Tiwari M et al., "Loss of Caspase-2-dependent Apoptosis Induces Autophagy after Mitochondrial Oxidative Stress in Primary Cultures of Young Adult Cortical Neurons", J Biol Chem 2011; 286: 8493-8506 (cited on p. 2).
Tiwari M et al., "A nonapoptotic role for CASP2/caspase 2", Autophagy 2014; 10: 1054-1070 (cited on p. 2).
Carlsson et al., "Genetic inhibition of caspase-2 reduces hypoxic-ischemic and excitotoxic neonatal brain injury", Annals of Neurology 2011, 70(5):781-9 (cited on p. 2).

(Continued)

*Primary Examiner* — D Margaret M Seaman
(74) *Attorney, Agent, or Firm* — Pearne & Gordon LLP

(57) ABSTRACT

The present invention relates to a compound of formula (I):

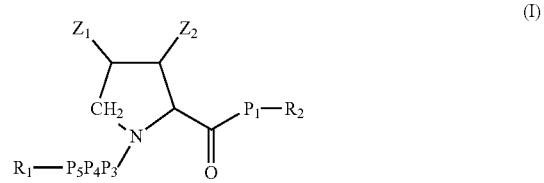

wherein $P_1$, $P_3$, $P_4$ and $P_5$ are amino acid residues or amino acid like structures.

The invention also relates to a compound of formula (I) for its use as a Caspase-2 inhibitor and for its therapeutical use. It also concerns the use of a compound of formula (I) as activity base probe to selectively detect Caspase-2 activity.

19 Claims, 1 Drawing Sheet

(56) References Cited

OTHER PUBLICATIONS

Thomas CN et al., "Caspase-2 Mediates Site-Specific Retinal Ganglion Cell Death After Blunt Ocular Injury", Invest Ophthalmol Vis Sci., Sep. 4, 2018; 59(11):4453-4462 (cited on p. 2).

Carol M. Troy et al. "Caspase-2 Mediates Neuronal Cell Death Induced by β-Amyloid", The Journal of Neuroscience, Feb. 15, 2000, 20(4):1386-1392 (cited on p. 2).

Ribe EM et al., "Neuronal caspase 2 activity and function requires RAIDD, but not PIDD", Biochem J. 2012 444 (3):591-9 (cited on p. 2).

Pozueta et al. "Caspase-2 is required for dendritic spine and behavioural alterations in J20 APP transgenic mice", Nat. Commun. 2013;4:1939 (cited on p. 3).

Zhao et al., "Caspase-2 cleavage of tau reversibly impairs memory", Nat. Med. 2016; 22 1268-1276 (cited on p. 3).

Machado et al., "Caspase-2 promotes obesity, the metabolic syndrome and nonalcholic fatty liver disease", Cell Death Dis. Feb. 18, 2016;7:e2096 (cited on p. 3).

Chauvier et al., "Targeting neonatal ischemic brain injury with a pentapeptide-based irreversible caspase inhibitor", Cell Death Dis 2011, 2:e203 (cited on p. 20).

Stine WB et al., "In Vitro Characterization of Conditions for Amyloid-β Peptide Oligomerization and Fibrillogenesis", (2003) in J Biol Chem 278,pp. 11612-11622 (cited on p. 41).

Deleglise B et al., "β-amyloid induces a dying-back process and remote trans-synaptic alterations in a microfluidic-based reconstructed neuronal network", Acta Neuropathol Commun. 2014;2: 145 (cited on p. 41).

Ahmed et al., "Ocular neuroprotection by siRNA targeting caspase-2", Cell Death and Disease, 2011, 2, e173,doi: 10.1038/cddis.2011. 54.

Carroll et al., "Mice lacking caspase-2 are protected from behavioral changes, but not pathology, in the YAC128 model of Huntington disease", Molecular Neurodegeneration, 2011,6:59.

Linton et al., "First-in-Class Pan Caspase Inhibitor Developed for the Treatment of Liver Disease", J. Med. Chem., 2005, 48, pp. 6779-6782.

* cited by examiner

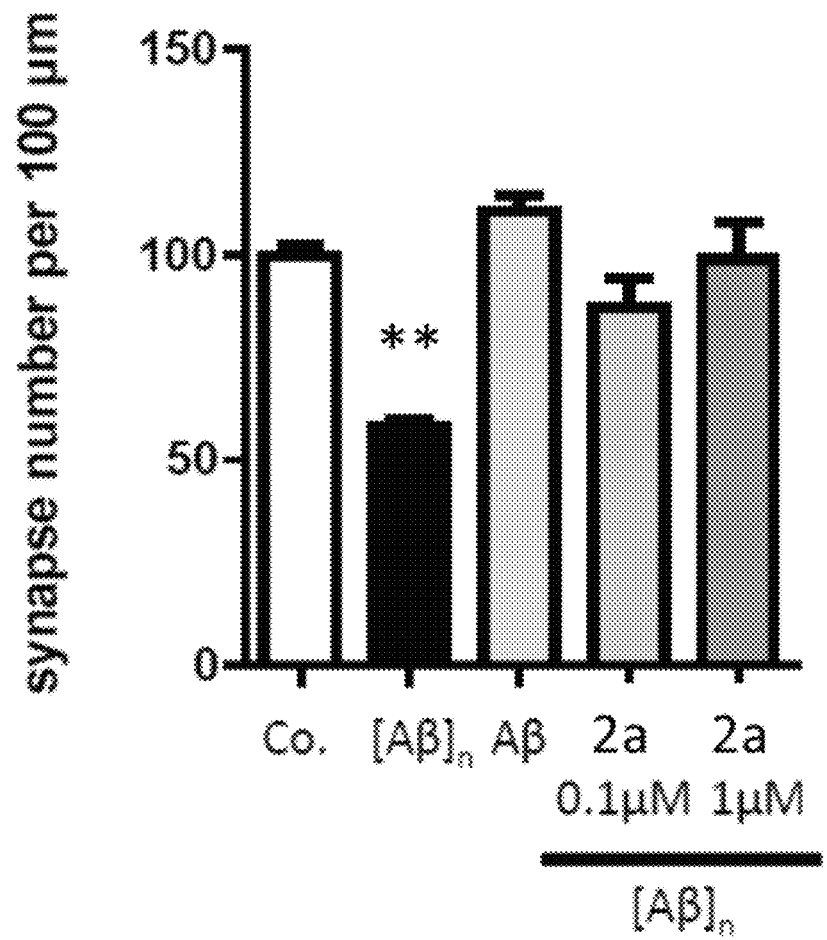

COMPOUNDS AND THEIR USE AS SELECTIVE INHIBITORS OF CASPASE-2

The present invention relates to novel compounds which are useful as selective inhibitors of Caspase-2. This invention also relates to the therapeutic use of these compounds and to their use as activity based probes (ABPs) for Caspase-2.

Caspases are a family of intracellular endoproteases using a cysteine residue at the initiation of the cleavage of peptide substrates. They are widely known to have important implications in the regulation of inflammation as well as a crucial role in the control of programmed cell death by apoptosis.

Caspases are classified in two major groups: those involved in the regulation of inflammatory processes (-1, -4, -5, -11, -12) and those that are central to the initiation and execution of apoptosis. There are two groups among apoptotic Caspases, the "initiators" who have a long N-terminal pro-domain (Caspase-2, -8, -9, -10), and those with a short pro-domain (residues 20-30) who are the "executors" of apoptosis (Caspase-3, -6, -7). Caspases involved in inflammation and the initiation of apoptosis have structural units involved in the transduction of the apoptotic signal, such as "Death Effector Domain" (DED) and "Caspase Recruitment Domain" (CARD). Each of these domains allows homotypic interaction with other protein partners.

The enzymatic properties of Caspases are governed by the existence of a catalytic dyad (cysteine, histidine) where cysteine acts as a nucleophile for the initiation of cleavage of peptide bonds. The active site of Caspases is highly conserved, with the catalytic cysteine included in a peptide sequence QACXG (where X is arginine (R), glutamine (Q) or glycine (G)) and a basic subsite S1, which gives them specificity for substrate cleavage after an aspartate residue, which is unique among mammalian proteases, except for the serine protease granzyme B. Generally, Caspases recognize a tetra-peptide motif, P1-P4 in N-ter of the cleavable bond, respectively recognized by subsites S1-S4 of the enzyme. The downstream positions Aspartate (P'1 and P'2) are also involved in the recognition and specificity vis-à-vis of Caspases.

Caspases have been classified in three groups based on the substrate peptide sequences they preferentially recognize. Group I Caspases (-1, -4 and -5) have a preference for a hydrophobic residue in P4. While the enzymes of group II (-2, -3, -7) have a strong preference for an Aspartate at this position, Group III (-6, -8, -9, -10) favors small aliphatic chains P4. In the group II, Caspase-2 has a unique recognition modality; indeed, it requires the recognition of a residue at position P5 (preferably a leucine, isoleucine, valine, or alanine) to exert its catalytic activity. Caspase-3 and -7 also recognize a P5 residue in a non-obligatory way.

Originally named Nedd-2, "Neural precursor cell Expressed developmentally down-regulated 2" in mice and Ich-1, "ICE and CED3 homolog" in humans, Caspase-2, encoded by the gene CASP2 (chr. 7q34-q35), is the most conserved member of this family of enzymes. Its activity is finely regulated during neuronal development in humans. There are two Caspase-2 isoforms: a proapoptotic one (2L) and an antiapoptotic one (2S). The 2L isoform is the predominant form in most tissues, but 2S isoform is expressed at similar levels in brain, skeletal muscle and heart.

Caspase-2 acts as an initiator Caspase that poorly cleaves other Caspases but can initiate mitochondrial outer membrane permeabilization, and that regulates diverse stress-induced signaling pathways including heat shock, DNA damage, mitochondria oxidative stress, and cytoskeleton disruption.

Beside apoptosis, Caspase-2 participates in the regulation of oxidative stress. For instance, elderly Casp-2$^{-/-}$ mice show reduced Superoxyde Dismutase and Gluthation peroxydase activities. In some specific circumstances, Caspase-2 can act as a tumor suppressor. Indeed, under oncogenic stress (as in the Ep-Myc transgenic mouse model), Caspase-2 deficiency potentiates tumorigenesis. Some data also suggest that Caspase-2 might inhibit autophagy (Tiwari M et al., J Biol Chem 2011; 286: 8493-8506; Tiwari M el al. Autophagy 2014; 10: 1054-1070).

Genetic inhibition of Caspase-2 was found to be neuroprotective in newborn mice exposed to hypoxic-ischemic or excitotoxic challenges, suggesting that Caspase-2-mediated cell death might contribute to the pathophysiology of perinatal brain injury (Carlsson et al., Annals of Neurology 2011, 70(5):781-9). In addition, genetic inhibition of Caspase-2 confers ocular neuroprotection (Amhed Z et al., Cell Death Dis. 2011 Jun. 16; 2:e173) and it has recently been shown that Caspase-2 mediates site-specific retinal ganglion Cell death after blunt ocular injury (Thomas C N et al., Invest Ophthalmol Vis Sci. 2018 Sep. 4; 59(11):4453-4462).

In cellular models of Alzheimer's disease (Carol M. Troy et al. The Journal of Neuroscience, Feb. 15, 2000, 20(4): 1386-1392), Caspase-2 is a key effector of neuronal death induced by the amyloid peptide Aβ (Ribe E M et al., Biochem J. 2012 444(3):591-9).

Moreover, using amyloid precursor protein transgenic mice, Pozueta et al. (*Nat. Commun.* 2013; 4:1939) have shown that:

(i) Caspase-2 is required for the cognitive decline in this Alzheimer animal model, (ii) cultured hippocampal neurons lacking Caspase-2 are immune to the synaptotoxic effects of Aβ, and (iii) Caspase-2 is a critical mediator in the activation of the RhoA/ROCK-II signaling pathway, leading to the collapse of dendritic spines, thus suggesting that Caspase-2 is a key driver of synaptic dysfunction in Alzheimer's disease.

Caspase-2 was also found to directly cleave the protein Tau and thus appears to be implicated in the generation of Δtau314, that might have an influence in synaptic dysfunction noticed in Alzheimer's disease and other tauopathies (Zhao et al. Nat. Med. 2016).

Caspase-2 seems also implicated in behavioral deficits in Huntington's disease (Caroli et al., Mol. Neurodegener. 2011 Aug. 19; 6:59).

Caspase-2 also appears to promote obesity, metabolic syndrome and nonalcoholic fatty liver disease. Indeed, it has been shown that Caspase-2 deficient mice were protected from these conditions (Machado M V et al. Cell Death Dis. 2016 Feb. 18; 7: e2096).

The first generations of Caspases inhibitors were aldehyde peptides which reversibly inhibit Caspases. Several sequences supposedly confer preferential effects vis-à-vis some members of the Caspase family have been developed including Ac-DEVD-CHO (a preferential inhibitor of Caspase-3 and Caspase-7) and Ac-VDVAD-CHO (a preferential inhibitor of Caspase-2, -3, and -7).

In the second generation of Caspases inhibitors, the aldehyde group has been replaced by α-substituted ketones with a fluoromethyl ketone group (fmk). This type of inhibitor inactivates the enzyme by forming an adduct with the active site cysteine. Z (Benzyloxylcarbonyle)-VAD-fmk is a broad-spectrum inhibitor of this generation. These molecules are toxic in vivo, because the release of fluoroacetate group, particularly in the liver, leads to the inhibition of aconitase. Thus, the development of inhibitors with a fmk group, was abandoned in the preclinical phase because of its hepatotoxicity. Then, several Caspase inhibitors have been synthetized in the art (Poreba et al., Chem Rev. 2015 Nov. 25; 115(22):12546-629). In particular, compounds able to inhibit Caspase-2 activity have been reported for example in WO 2005/105829 and EP2670774. However, these known Caspase-2 inhibitors also have a too high activity with respect to Caspase-3. They thus cannot be qualified as selective Caspase-2 inhibitors.

More recently, a series of reversible Caspase-2 inhibitor has been reported. When evaluated in vitro on human recombinant Caspases, these compounds were found to preferentially inhibit Caspase-2, but have moderate effects in cellular assays and structural properties that are incompatible with in vivo use (Maillard et al., Biorganic &Medicinal Chemistry 19 (2011) 5833-5851).

Accordingly, there is still a need for potent and selective Caspase-2 inhibitors more particularly with a significantly reduced activity against Caspase-3. In particular, it would be highly advantageous to provide more selective and efficient Caspase-2 inhibitors for use in the prevention and/or treatment of diseases and/or injuries in which Caspase-2 activity is implicated such as neonatal brain ischemia, heart ischemia and chronic degenerative diseases like for instance Alzheimer's disease.

It would also be very advantageous to provide more efficacious and selective Caspase-2 inhibitors for use as an activity-based probe to specifically detect Caspase-2 activity.

The compounds of the invention aim to meet these needs.

Thus, according to one of its aspects, the present invention relates to a compound of formula (I):

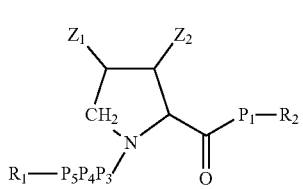
(I)

in which:
Z$_1$ and Z$_2$, identical or different are selected from a hydrogen atom, a (C$_1$-C$_6$)alkyl and a (C$_1$-C$_6$)alkoxy group;
P$_5$ is selected from the following amino acid residues or amino acid like structures:

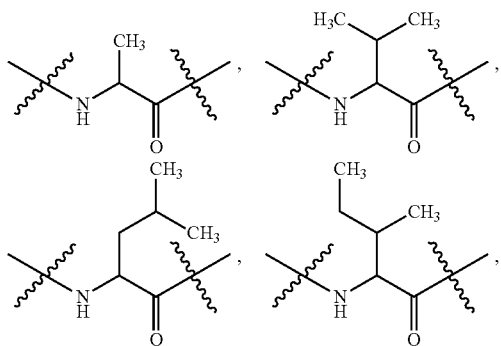

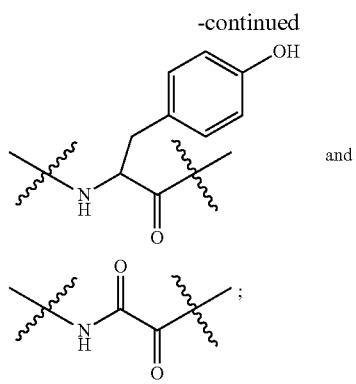

P$_1$ and P$_4$, identical or different, are selected from the following amino acid like structures:

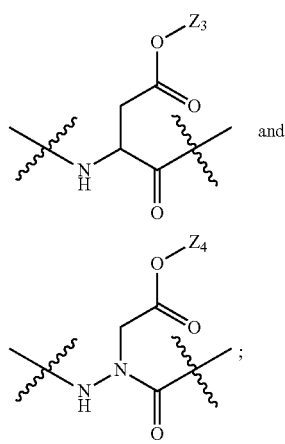

in which Z$_3$ and Z$_4$, identical or different, are selected from a hydrogen atom and a (C$_1$-C$_6$)alkyl group;

P$_3$ is selected from the following amino acid residues:

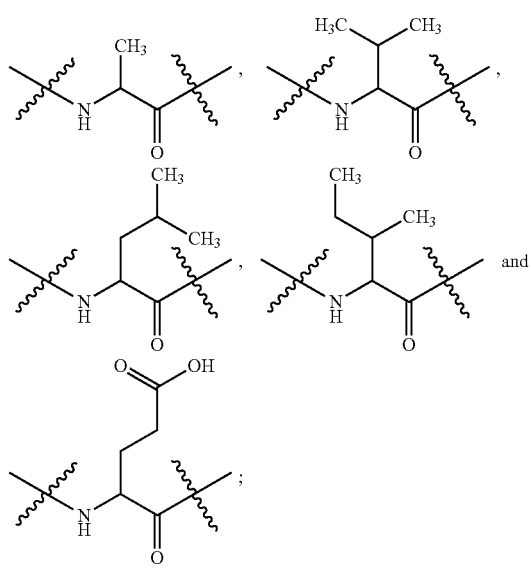

$R_1$ is selected from

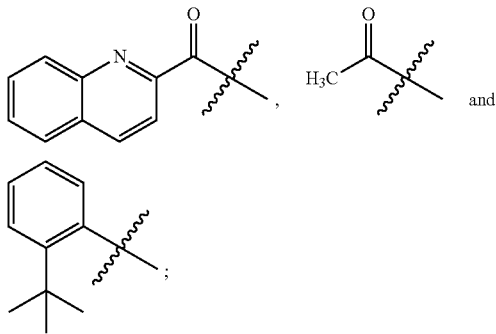

and $R_2$ is selected from:

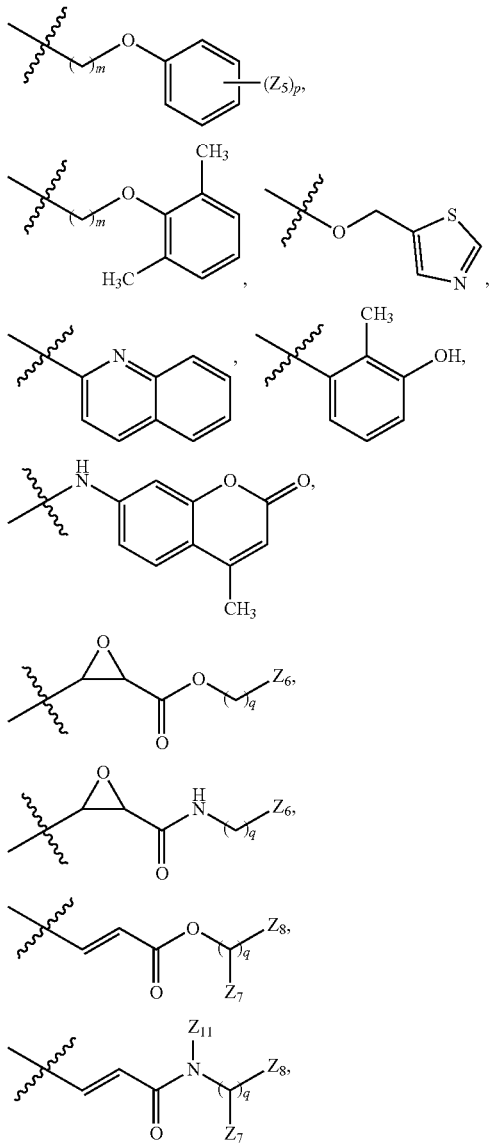

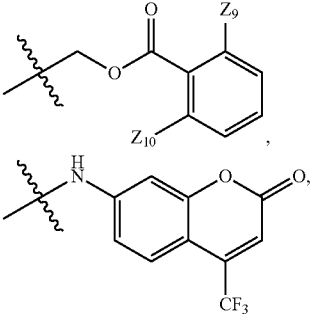

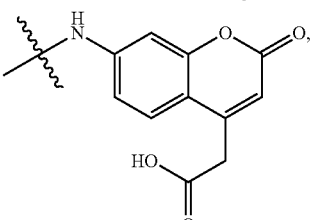

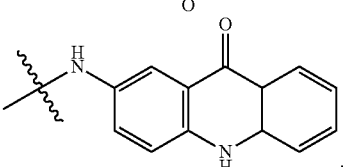

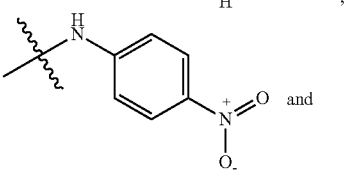

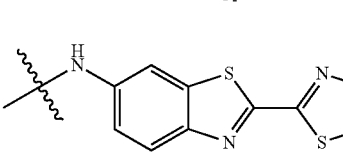

in which
  m is 0, 1 or 2;
  p is 1, 2, 3 or 4;
  $Z_5$ is a halogen atom;
  q is 0 or 1;
  $Z_6$ is selected from a $(C_1\text{-}C_6)$alkyl and a phenyl group, said phenyl group being optionally substituted by an amino group;
  $Z_7$, $Z_8$ and $Z_{11}$, identical or different, are selected from a hydrogen atom, a $(C_1\text{-}C_4)$alkyl, a tetrahydroquinolynyl and a $-(CH_2)_i$-aryl group with i being 0, 1 or 2, said aryl group being optionally substituted by one, two, three, or four halogen atom(s) or one $(C_1\text{-}C_4)$ alkyl group; and
  $Z_9$ and $Z_{10}$, identical or different, are selected from a halogen atom and a $(C_1\text{-}C_6)$alkyl group;
  or one of its salts;
said compound of formula (I) being in all the possible racemic, enantiomeric and diastereoisomeric isomer forms.

After extensive research, the inventor has found that these compounds of formula (I) acts as selective and effective inhibitors of Caspase-2 activity as demonstrated in the following examples.

Indeed, the compounds of the present invention are much more efficient to inhibit Caspase-2 than to inhibit Caspase-3.

In particular, as shown in the following examples, some compounds of the invention exhibit an inhibitory effect on Caspase-2 at least two times, preferably at least 5 times, more preferably at least 10 times, and even more preferably at least 15 times higher than their inhibitory effect on Caspase-3.

The inhibitory effect of the compounds of the invention with respect to Caspase-2 and Caspase-3 may be evaluated by kinetic approaches using human recombinant Caspases. For irreversible inhibitors, $k_{inact}/K_I$ ratio is determined using the method disclosed in example 2. For reversible inhibitors $IC_{50}$ and $k_i$ are determined.

Moreover, the fact that some of these inhibitors are irreversible is very advantageous since this type of inhibitors can be used in prolonged suppression of Caspase-2, limited only by the normal rate of protein resynthesis, also called turnover.

In the meaning of the present invention:
- A "Caspase inhibitor" is intended to mean a compound that reduces or suppresses the activity of the targeted Caspase, as compared with said activity determined without said inhibitor.
- A "selective Caspase-2 inhibitor" is intended to mean a compound that decreases the activity of Caspase-2 more than the activity of other Caspases, in particular Caspase-3.

Thus, according to a second aspect, the invention is directed to a compound of the invention for its use as selective Caspase-2 inhibitor.

According to one embodiment, the $R_2$ radical of the compounds of the invention is selected from:

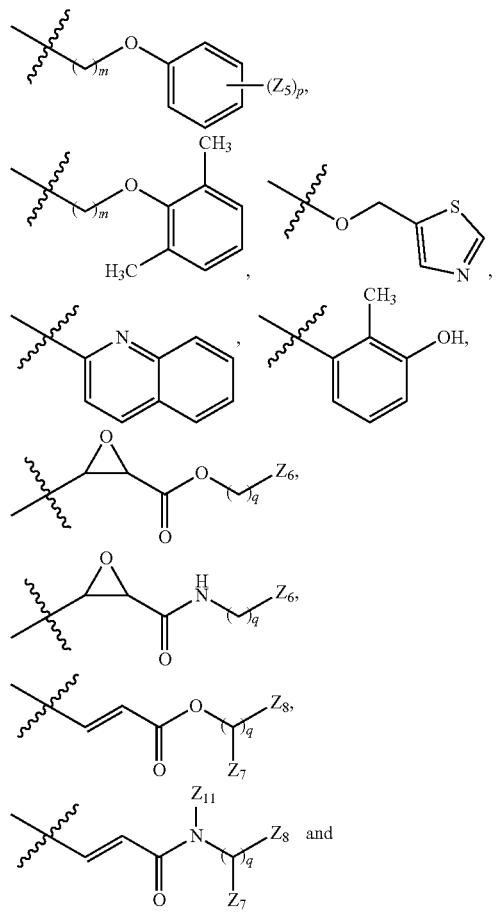

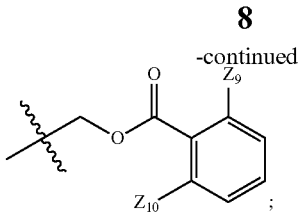

in which m, p, q, $Z_5$, $Z_6$, $Z_7$, $Z_8$, $Z_9$, $Z_{10}$ and $Z_{11}$ are as above defined.

These compounds may advantageously be introduced in a pharmaceutical composition. These compounds may be used as a medicament. More particularly, they may be used in the prevention and/or treatment of diseases and/or injuries in which Caspase-2 activity is implicated.

For the purposes of the present invention the term "prevention" means at least partly reducing the risk of manifestation of a given phenomenon, i.e., in the present invention, a disease and/or injury in which Caspase-2 activity is implicated. A partial reduction implies that the risk remains, but to a lesser extent than before implementing the invention.

For the purposes of the present invention the term "treatment" is intended to mean completely or partially curing a given phenomenon, i.e., in the present invention, a disease and/or injury in which Caspase-2 activity is implicated, including decreasing, minimizing or reducing said given phenomenon.

Thus, according to a third aspect, the invention is directed to a pharmaceutical composition comprising at least one compound of the invention wherein $R_2$ is as above defined and at least one pharmaceutically acceptable excipient.

According to a fourth aspect, the invention is directed to a compound of the invention wherein $R_2$ is as above defined, for its use as a medicament.

According to a fifth aspect, the invention is directed to a compound of the invention wherein $R_2$ is as above defined, for its use in the prevention and/or treatment of diseases and/or injuries in which Caspase-2 activity is implicated.

According to a sixth aspect, the invention is directed to a compound of the invention wherein $R_2$ is as above defined, for its use in protecting neuronal cells from Aβ-induced dysfunction or toxicity, more particularly against Aβ-induced cell death, Aβ-induced axonal degeneration, Aβ-induced electrophysiological dysfunction, and/or Aβ-induced synapse loss.

According to another embodiment, the $R_2$ radical of the compounds of the invention is selected from:

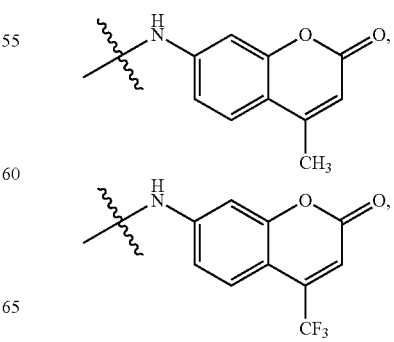

-continued

[chemical structures]

These compounds may advantageously be used as an activity-based probe to selectively detect Caspase-2 activity.

Thus, according to a sixth aspect, the invention is directed to the use of a compound of the invention wherein $R_2$ is as above defined, as an activity-based probe to selectively detect Caspase-2 activity.

In the context of the present invention, the following abbreviations and empirical formulae are used:
Boc Tert-Butyloxycarbonyl
° C. Degree Celsius
Me Methyl
Bn Benzyl
AMC 7-amino-4-methylcoumarin
PBS Phosphate Buffered Saline
Ac Acetyl
RFU Relative Fluorescence Units
HEPES 4-(2-hydroxyethyl)-1-piperazineethanesulfonic acid
DTT Dithiothreitol
EDTA Ethylenediaminetetraacetic acid
CHAPS (3-((3-cholamidopropyl) dimethylammonio)-1-propanesulfonate)
DMSO Dimethyl sulfoxide It should further be noted that in all amino-acid like sequences that are represented in the present invention by using the above-mentioned abbreviations, the left and right orientation is in the conventional direction of amino-terminus to carboxy-terminus.

Accordingly, it appears clearly that in a formula defining a peptide like structure according to the invention, when a sequence as $R_1$—$P_5P_4P_3$— or —$P_1$—$R_2$ is indicated:

(i) the

[structure]

part of the $P_5$ amino acid residue or amino acid like residue is linked to $R_1$;
the one of the $P_4$ amino acid like residue is linked to the $P_5$ amino acid residue or amino acid like residue;
the one of the P3 amino acid residue is linked to the $P_4$ amino acid like residue; and
the one of the $P_1$ amino acid like residue is linked to

[structure]

at the opposite of $R_2$ as represented in formula (I); and (ii) the

[structure]

part of the $P_5$ amino acid residue or amino acid like residue is linked to the $P_4$ amino acid like residue;
the one of the $P_4$ amino acid like residue is linked to the $P_3$ amino acid residue;
the one of the $P_3$ amino acid residue is linked to the

[structure]

at the opposite of the $P_4$ amino acid like residue as represented in formula (I); and
the one of the $P_1$ amino acid like residue is linked to $R_2$.

Other features and advantages of the invention will emerge more clearly from the description, and the examples which follow given by way of non-limiting illustration.

FIGURE

FIG. 1: Synapse protection toward Amyloid beta peptide [1-42] oligomers toxicity with compound 2. Co: control; $[A\beta]_n$: Neurons intoxicated with Amyloid beta peptide [1-42] oligomers, 10 nM; Aβ: Neurons incubated with non-oligomeric (non toxic) Amyloid beta, 10 nM; 2a: Neurons intoxicated with Amyloid beta peptide [1-42] oligomers, 10 nM but pretreated with compound 2 enantiomer a at 0.1 µM or 1 µM (**$p<0.01$ (Kruskall-Wallis Dunn's post hoc test)).

COMPOUNDS OF THE INVENTION

As above-mentioned, the compounds according to the invention correspond to general formula (I):

[structure (I)]

in which:

Z$_1$ and Z$_2$, identical or different are selected from a hydrogen atom, a (C$_1$-C$_6$)alkyl and a (C$_1$-C$_6$)alkoxy group;

P$_5$ is selected from the following amino acids residues or amino acid like structures:

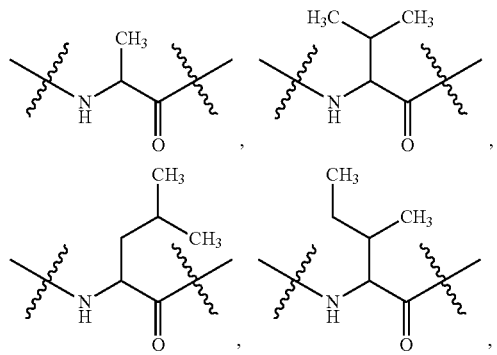

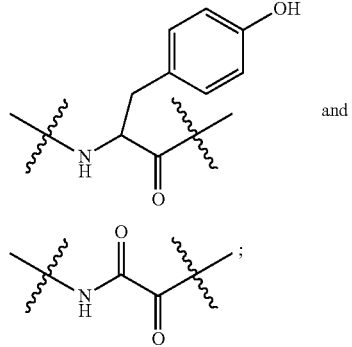

P$_1$ and P$_4$, identical or different, are selected from the following amino acid like structures compounds:

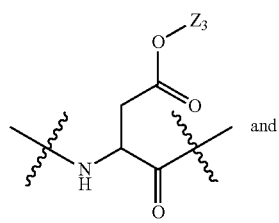

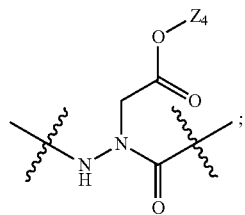

in which Z$_3$ and Z$_4$, identical or different, are selected from a hydrogen atom and a (C$_1$-C$_6$)alkyl group;

P$_3$ is selected from the following amino acid residues:

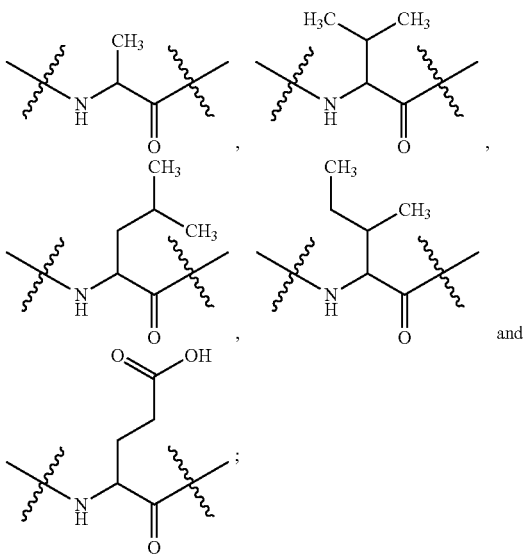

R$_1$ is selected from:

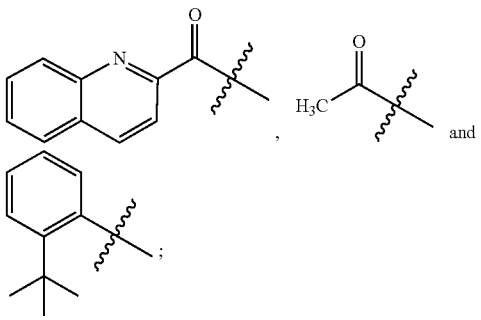

and

R$_2$ is selected from:

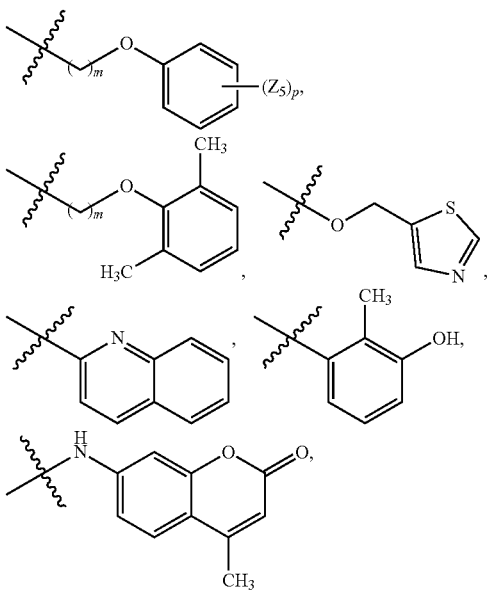

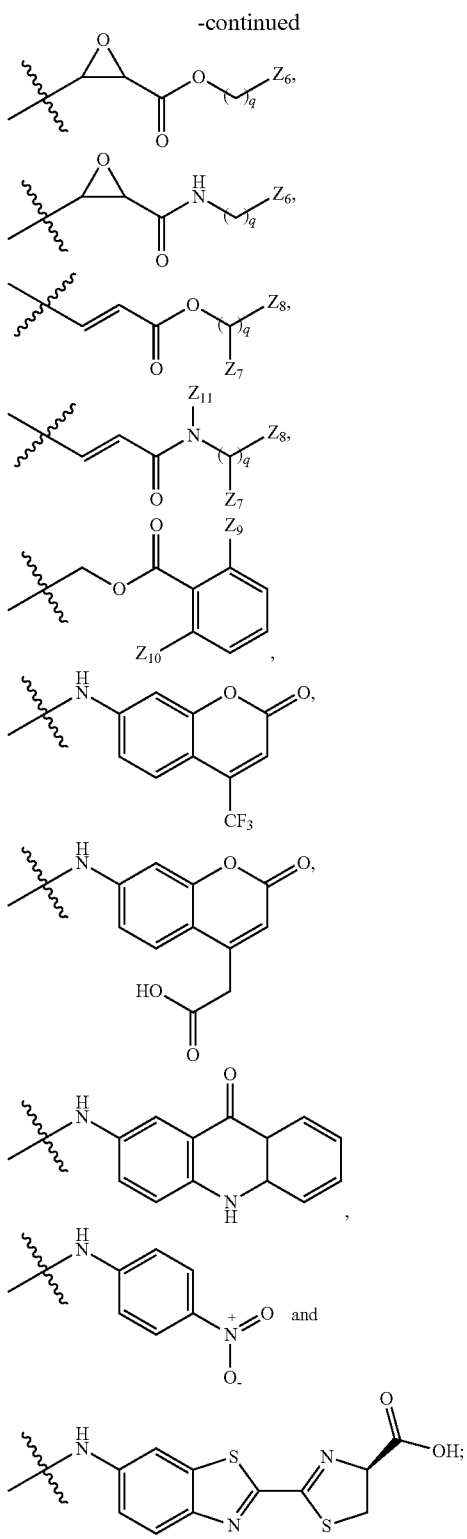

in which:
m is 0, 1 or 2;
p is 1, 2, 3 or 4;
$Z_5$ is a halogen atom;
q is 0 or 1;
$Z_6$ is selected from a $(C_1-C_6)$alkyl and a phenyl group, said phenyl group being optionally substituted by an amino group;

$Z_7$, $Z_8$ and $Z_{11}$, identical or different, are selected from a hydrogen atom, a $(C_1-C_4)$alkyl, a tetrahydroquinolynyl and a —$(CH_2)_i$-aryl group with i being 0, 1 or 2, said aryl group being optionally substituted by one, two, three, or four halogen atom(s) or one $(C_1-C_4)$ alkyl group; and $Z_9$ and $Z_{10}$, identical or different, are selected from a halogen atom and a $(C_1-C_6)$alkyl group;

or one of its salts;
said compound of formula (I) being in all the possible racemic, enantiomeric and diastereoisomeric isomer forms.

In a particular embodiment, the asymmetric carbon atom of pyrrolidine ring linked to

is of (S) configuration, and the other asymmetric alpha carbons of amino acid like P1, P3, $P_4$ and P5 are of (S) configuration.

In yet a particular embodiment, the asymmetric carbon atom of pyrrolidine ring linked to

is of (R) configuration, and the other asymmetric alpha carbons of amino acid like P1, P3, $P_4$ and P5 are of (S) configuration.

Accordingly, the compounds of the invention comprise several asymmetric carbon atoms. They thus may exist in the form of enantiomers or diastereoisomers. These enantiomers and diastereoisomers, and also mixtures thereof, including racemic mixtures, form part of the invention.

The compounds of the invention may also exist in the form of bases or of acid-addition salts. These salts may be prepared with pharmaceutically acceptable acids, but the salts of other acids that are useful, for example, for purifying or isolating the compounds of formula (I) also form part of the invention.

The term "pharmaceutically acceptable" means what is useful in preparing a pharmaceutical composition generally safe, non-toxic, and neither biologically nor otherwise undesirable and includes what is acceptable for veterinary as well as human pharmaceutical use.

The compounds of the invention may also exist in the form of hydrates or solvates, i.e. in the form of associations or combinations with one or more molecules of water or with a solvent. Such hydrates and solvates also form part of the invention.

In the context of the present invention, the following definitions apply:
a halogen atom: a fluorine, a chlorine, a bromine or an iodine atom. The halogen atoms may be more particularly fluorine atoms.

$C_t-C_z$: a carbon-based chain possibly containing from t to z carbon atoms in which t and z may take values from 1 to 10; for example, $C_1-C_3$ is a carbon-based chain possibly containing from 1 to 3 carbon atoms.

an alkyl: a linear or branched saturated aliphatic group, in particular comprising form 1 to 6 carbon atoms.

Examples that may be mentioned include methyl, ethyl, n-propyl, isopropyl, butyl, isobutyl, tert-butyl, pentyl, neopenthyl etc.

an alkoxy: a radical —O-alkyl in which the alkyl group is as defined previously.

an aryl: a monocyclic or bicyclic aromatic group containing between 5 and 10 carbon atoms, in particular between 6 and 10 carbon atoms. By way of examples of an aryl group, mention may be made of phenyl or naphthyl group. Preferably, the aryl group is phenyl.

Among the compounds of general formula (I) according to the invention, a subgroup of compounds is constituted by the compounds of formula (II):

(II)

wherein:
- $R_1$ and $R_2$ are as defined in the formula (I);
- $Z_1$ and $Z_2$ are as defined in the formula (I);
- $R_3$ is selected from a —$CH_3$, a —$CH(CH_3)_2$, a —$CH_2CH(CH_3)_2$, a —$CH(CH_3)CH_2CH_3$ and a 4-hydroxyphenyl group;
- A and B, identical or different, are selected from a nitrogen atom and a —CH— group;
- $R_5$ and $R_6$, identical or different, are selected from a hydrogen atom and a ($C_1$-$C_6$)alkyl group; and
- $R_4$ is selected from a —$CH_3$, a —$CH(CH_3)_2$, a —$CH_2CH(CH_3)_2$, a —$CH(CH_3)CH_2CH_3$ and a —$(CH_2)_2CO_2H$ group;

or one of its salts;
said compound of formula (II) being in all the possible racemic, enantiomeric and diastereoisomeric isomer forms.

In a particular embodiment, the asymmetric carbon atom of pyrrolidine ring linked to is of (S) configuration and the other asymmetric alpha carbons of amino acid like P1, P3, $P_4$ and P5 are of (S) configuration.

In yet a particular embodiment, the asymmetric carbon atom of pyrrolidine ring linked to is of (R) configuration and the other asymmetric alpha carbons of amino acid like P1, P3, $P_4$ and P5 are of (S) configuration.

Preferably in formula (II), at least one of A and B is a —CH group, more preferably A and B are —CH groups.

According to a preferred mode of the invention, the compounds according to the invention may be of formula (III):

(III)

wherein $R_1$ and $R_2$ are as defined in the formula (I);
or one of its salts;

said compound of formula (III) being in all the possible racemic, enantiomeric and diastereoisomeric isomer forms.

According to another preferred embodiment, in formula (I), (II) and/or (III), $R_1$ is:

According to another preferred embodiment, in formula (I), (II) and/or (III), $R_1$ is:

According to another preferred embodiment, in formula (I), (II) and/or (III), $R_2$ is selected from:

17
-continued

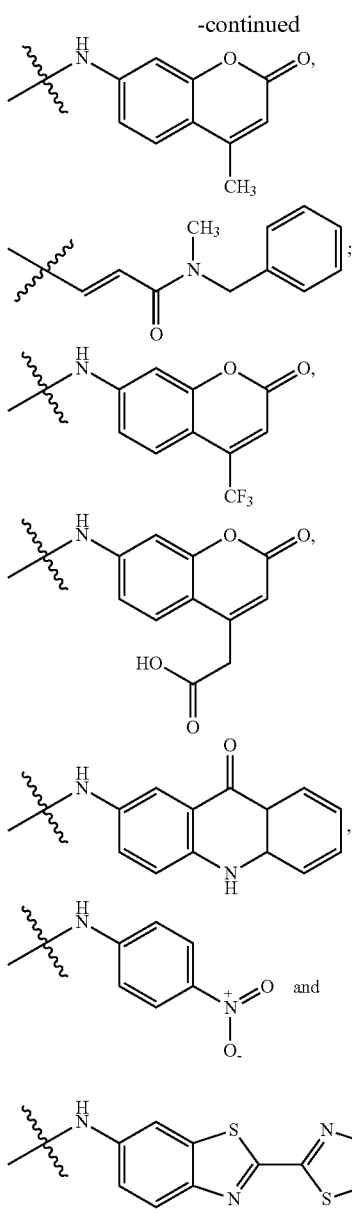

in which Z' is a fluorine atom and j is 0, 1 or 2.

18

Preferably, $R_2$ is:

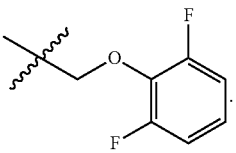 [SMILES: *COc1c(F)cccc1F]

In a particular embodiment, when $R_2$ is a methoxyphenyl as defined above, the phenyl ring is substituted with 2, 3, 4 or 5 halogen atoms, preferably said halogen is selected from fluorine or chlorine atoms.

According to yet a preferred embodiment, the compounds according to the invention have at least one, preferably at least three asymmetric carbon atoms of (S) configuration.

In a particular embodiment, the asymmetric carbon atom of pyrrolidine ring linked to

is of (S) configuration and the other asymmetric alpha carbons of amino acid like P1, P3, P4 and P5 are of (S) configuration.

More preferably, all the asymmetric carbon atoms of the compounds according to the invention are of (S) configuration.

In yet a particular embodiment, the asymmetric carbon atom of pyrrolidine ring linked to

is of (R) configuration and the other asymmetric alpha carbons of amino acid like P1, P3, P4 and P5 are of (S) configuration.

Among the compounds of general formula (I) according to the invention, mention may be made especially of the following compounds:

| STRUCTURE/Compound No | IUPAC NAME |
|---|---|
| 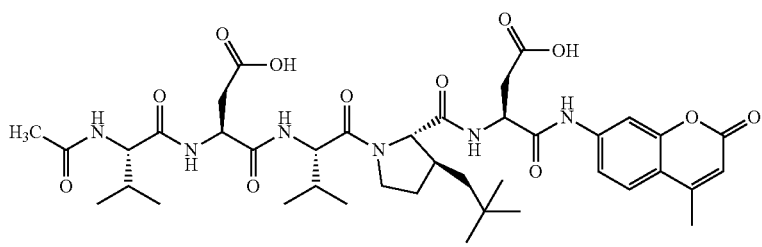<br>1 | (S)-3-((S)-2-acetamido-3-methylbutanamido)-4-(((S)-1-((2S,3S)-2-(((S)-3-carboxy-1-((4-methyl-2-oxo-2H-chromen-7-yl)amino)-1-oxopropan-2-yl)carbamoyl)-3-neopentylpyrrolidin-1-yl)-3-methyl-1-oxobutan-2-yl)amino)-4-oxobutanoic acid |

| STRUCTURE/Compound No | IUPAC NAME |
|---|---|
| 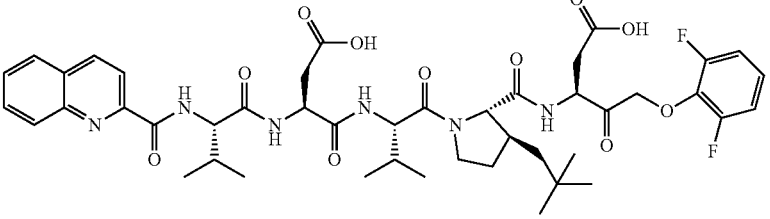<br>2 | (S)-4-(((S)-1-((2S,3S)-2-(2-(carboxymethyl)-2-(2-(2,6-difluorophenoxy)acetyl)hydrazinecarbonyl)-3-neopentylpyrrolidin-1-yl)-3-methyl-1-oxobutan-2-yl)amino)-3-((S)-3-methyl-2-(quinoline-2-carboxamido)butanamido)-4-oxobutanoic acid |
| 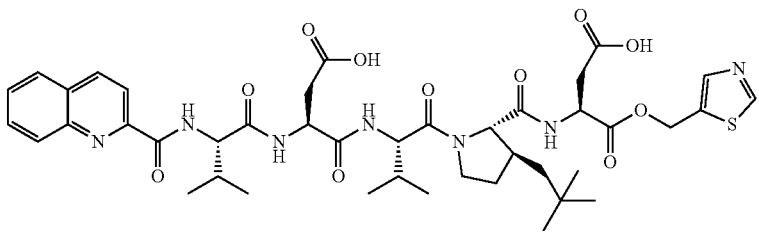<br>3 | (S)-4-(((S)-1-((2S,3S)-2-(((S)-3-carboxy-1-oxo-1-(thiazol-5-ylmethoxy)propan-2-yl)carbamoyl)-3-neopenthylpyrrolidin-1-yl)-3-methyl-1-oxobutan-2-yl)amino)-3-((S)-3-methyl-2-(quinoline-2-carboxamido)butanamido)-4-oxobutanoic acid |
| 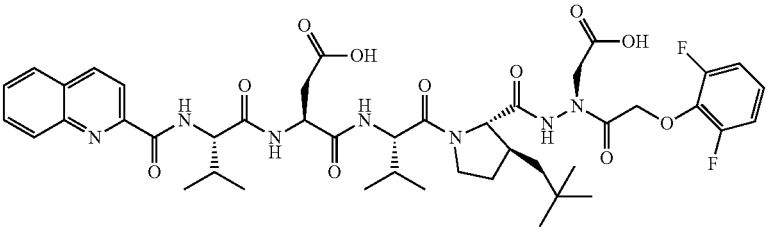<br>4 | (S)-4-(((S)-1-((2S,3S)-2-(2-(carboxymethyl)-2-(2-(2,6-difluorophenoxy)acetyl)hydrazinecarbonyl)-3-neopentylpyrrolidin-1-yl)-3-methyl-1-oxobutan-2-yl)amino)-3-((S)-3-methyl-2-(quinoline-2-carboxamido)butanamido)-4-oxobutanoic acid |
| 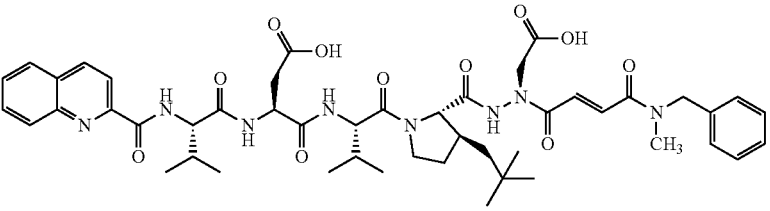<br>5 | (S)-4-(((S)-1-((2S,3S)-2-(2-((E)-4-(benzyl(methyl)amino)-4-oxobut-2-enoyl)-2-(carboxymethyl)hydrazinecarbonyl)-3-neopentylpyrrolidin-1-yl)-3-methyl-1-oxobutan-2-yl)amino)-3-((S)-3-methyl-2-(quinoline-2-carboxamido)butanamido)-4-oxobutanoic acid |
| 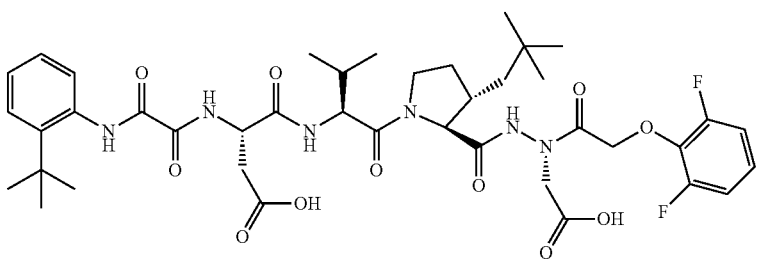<br>6 | (S)-3-(2-((2-(tert-butyl)phenyl)amino)-2-oxoacetamido)-4-(((S)-1-((2S,3S)-2-(2-(carboxymethyl)-2-(2-(2,6-difluorophenoxy)acetyl)hydrazinecarbonyl)-3-neopentylpyrrolidin-1-yl)-3-methyl-1-oxobutan-2-yl)amino)-4-oxobutanoic acid |

Accordingly, in a particular embodiment, a compound according to the invention is selected from compounds 1 to 6 indicated here-above.

Preparation of the Compounds of the Invention

The compounds of the invention may be prepared by organic and peptide synthesis. Assembly of the structure by peptide synthesis belongs to the general knowledge of the skilled artisan and further details are depicted in Linton et al., J. Med. Chem. 2005, 48, 6779-6782 and in Chauvier et al Cell Death Dis 2011, 2:e203. The precursors of $R_1$, $R_2$, $P_1$, X, $P_3$, $P_4$ and $P_5$ that lead to the compounds of the invention are introduced in the different steps of the process.

The precursor may either be commercial product or commercial product that has been functionalized according to well-known protocols for the skilled artisan. Further details and references can be made to "Design of Caspase inhibitors as potential clinical agents; CRC press; CRC Enzyme inhibitors series, Edited by Tom O'Brien & Steven D. Linton chapter 7 by BR Ullman".

In particular, example 1 of the present invention illustrates the protocol of preparation of the compound 2 according to the invention.

Applications

As specified previously and clearly illustrated by the following examples, the compounds according to the present invention are useful as selective Caspase-2 inhibitors.

Indeed, as pointed out by the examples they show a much better inhibitory effect for Caspase-2 than for Caspase-3 despite that these two have closest resembling active site among all the caspases. As a consequence, they are efficient to selectively inhibit Caspase-2.

a) Therapeutic Field

In view of the above, the compounds of the present invention, and more particularly the compounds for which the $R_2$ radical is selected from:

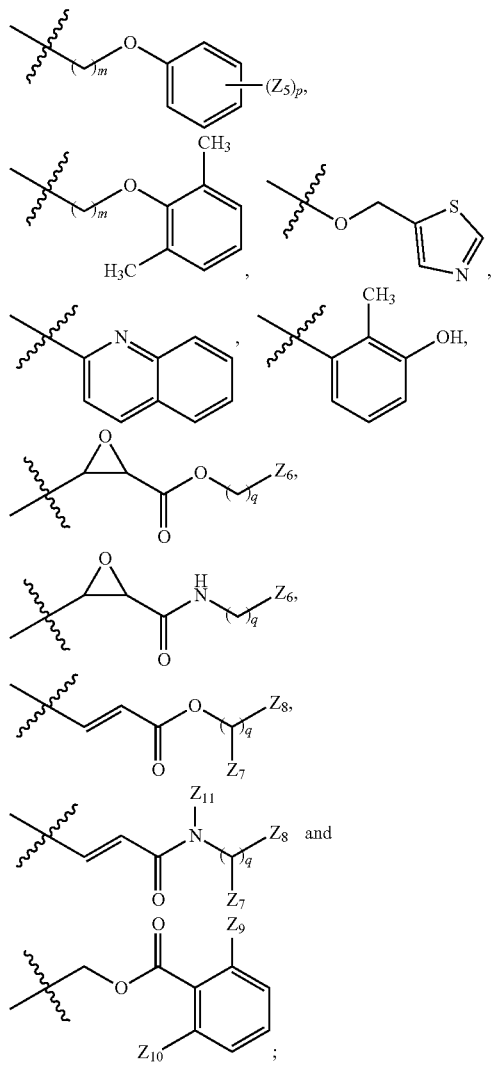

in which m, p, q, $Z_5$, $Z_6$, $Z_7$, $Z_8$, $Z_9$, $Z_{10}$ and $Z_{11}$ are as above defined, may be used in the therapeutic field.

According to one of its aspects, the present invention therefore relates to a compound of the invention wherein $R_2$ is as above defined, for its use as a medicament, in particular a medicament intended to selectively inhibit the activity of Caspase-2.

In other terms, the invention concerns the use of a compound according to the invention in which $R_2$ is as above defined for the preparation of a medicine, in particular of a drug for selectively inhibiting the activity of Caspase-2.

In other words, the present invention relates to a medicament comprising at least one compound according to the invention in which $R_2$ is as above defined, in particular a medicament for selectively inhibiting the activity of Caspase-2.

Thus, according to another of its aspects, the invention is directed to a compound of the invention wherein $R_2$ is as above defined, for its use in the prevention and/or treatment of diseases and/or injuries in which Caspase-2 activity is implicated.

In other terms, the invention concerns the use of a compound according to the invention in which $R_2$ is as above defined for the preparation of a medicament intended to prevent and/or treat diseases and/or injuries in which Caspase-2 activity is implicated.

In particular, said diseases and/or injuries may be selected among pathologies with cell death, particularly among:
chronic degenerative diseases such as Alzheimer's disease or other Tauopathies, Huntington's disease and Parkinson's disease;
neonatal brain damage in particular neonatal brain ischemia;
traumatic brain injury;
kidney ischemia;
hypoxia-ischemia (H-I) injuries;
stroke-like situations brain injuries;
heart ischemia;
myocardial infarction;
amyotrophic lateral sclerosis (ALS);
retinal damages;
ophthalmic diseases such as blunt ocular injury, ischemic optic neuropathy and glaucoma;
skin damages;
sterile inflammatory diseases such as diabetes, atherosclerosis, cardiac ischemia, gout, pseudogout, joint loosening, atherosclerosis, syndromes triggered by aluminium salts, non-arteritic ischemic optic neuropathy (NAION), glaucoma and metabolic diseases;
non-sterile inflammatory diseases such as bacterial infection in particular with bacteria producing pore-forming toxins, influenza virus infection and single-stranded (ss) RNA Rhabdoviridae infection such as Maraba virus or vesicular stomatitis virus (VSV);
diseases caused by pathogenic bacteria, such as *Brucella*, *Staphylococcus aureus* and *Salmonella*;
dyslipidemias;
obesity;
metabolic syndrome; and
nonalcoholic fatty liver disease.

More particularly, said diseases and/or injuries are selected from chronic neurodegenerative diseases. Preferably they are chosen among Alzheimer's disease, other known tauopathies (as primary age-related tauopathy, chronic traumatic encephalopathy, progressive supranuclear palsy, corticobasal degeneration, frontotemporal dementia, parkinsonism linked to chromosome 17, Lytico-Bodig disease, ganglioglioma and gangliocytoma, meningioangiomatosis, postencephalitic parkinsonism, subacute sclerosing panencephalitis, lead encephalopathy, tuberous sclerosis, antothenate kinase-associated neurodegeneration, lipofuscinosis), Huntington's disease and Parkinson's disease, more specifically Alzheimer's disease.

According to another aspect, the invention is directed to a compound of the invention wherein $R_2$ is as above defined, for its use in synaptoprotection, more particularly in the prevention and/or treatment of neurodegenerative diseases, even more particularly of Alzheimer's Disease or of tauopathies.

In an embodiment of the invention, the invention is directed to a compound selected from compound 2, compound 3, compound 4, compound 5 and/or compound 6 as defined above for its use in the prevention and/or treatment of Alzheimer's disease or other Tauopathies.

In a further embodiment, the invention is directed to compound 2 as defined above for its use in the prevention and/or treatment of Alzheimer's disease or other Tauopathies.

In a further embodiment, the invention is directed to compound 3 as defined above for its use in the prevention and/or treatment of Alzheimer's disease or other Tauopathies.

In a further embodiment, the invention is directed to compound 4 as defined above for its use in the prevention and/or treatment of Alzheimer's disease or other Tauopathies.

In a further embodiment, the invention is directed to compound 5 as defined above for its use in the prevention and/or treatment of Alzheimer's disease or other Tauopathies.

In a further embodiment, the invention is directed to compound 6 as defined above for its use in the prevention and/or treatment of Alzheimer's disease or other Tauopathies.

In a particular embodiment, the present invention relates to a compound as defined above for its use in the prevention and/or treatment of Alzheimer's disease.

In an embodiment of the invention, the invention is directed to a compound selected from compound 2, compound 3, compound 4, compound 5 and/or compound 6 as defined above for its use in the prevention and/or treatment of Alzheimer's disease.

In a further embodiment, the invention is directed to compound 2 as defined above for its use in the prevention and/or treatment of Alzheimer's disease.

In a further embodiment, the invention is directed to compound 3 as defined above for its use in the prevention and/or treatment of Alzheimer's disease.

In a further embodiment, the invention is directed to compound 4 as defined above for its use in the prevention and/or treatment of Alzheimer's disease.

In a further embodiment, the invention is directed to compound 5 as defined above for its use in the prevention and/or treatment of Alzheimer's disease.

In a further embodiment, the invention is directed to compound 6 as defined above for its use in the prevention and/or treatment of Alzheimer's disease.

Even more particularly, as shown in the experimental section, compound of the invention in which $R_2$ is as above defined are effective in protecting neuronal cells from Aβ oligomer induced dysfunction or toxicity.

Accordingly, according to a further aspect, the invention is directed to a compound of the invention wherein $R_2$ is as above defined, for its use in protecting neuronal cells from Aβ-induced dysfunction or toxicity, more particularly against Aβ-induced cell death, Aβ-induced axonal degeneration, Aβ-induced electrophysiological dysfunction and/or Aβ-induced synapse loss.

In an embodiment of the invention, the invention is directed to a compound selected from compound 2, compound 3, compound 4, compound 5 and/or compound 6 as defined above for its use in protecting neuronal cells from Aβ-induced dysfunction or toxicity, more particularly against Aβ-induced cell death, Aβ-induced axonal degeneration, Aβ-induced electrophysiological dysfunction, and/or Aβ-induced synapse loss.

In a further embodiment, the invention is directed to compound 2 as defined above for its use in protecting neuronal cells from Aβ-induced dysfunction or toxicity, more particularly against Aβ-induced cell death, Aβ-induced axonal degeneration, Aβ-induced electrophysiological dysfunction, and/or Aβ-induced synapse loss.

In a further embodiment, the invention is directed to compound 3 as defined above for its use in protecting neuronal cells from Aβ-induced dysfunction or toxicity, more particularly against Aβ-induced cell death, Aβ-induced axonal degeneration, Aβ-induced electrophysiological dysfunction, and/or Aβ-induced synapse loss.

In a further embodiment, the invention is directed to compound 4 as defined above for its use in protecting neuronal cells from Aβ-induced dysfunction or toxicity, more particularly against Aβ-induced cell death, Aβ-induced axonal degeneration, Aβ-induced electrophysiological dysfunction, and/or Aβ-induced synapse loss.

In a further embodiment, the invention is directed to compound 5 as defined above for its use in protecting neuronal cells from Aβ-induced dysfunction or toxicity, more particularly against Aβ-induced cell death, Aβ-induced axonal degeneration, Aβ-induced electrophysiological dysfunction, and/or Aβ-induced synapse loss.

In a further embodiment, the invention is directed to compound 6 as defined above for its use in protecting neuronal cells from Aβ-induced dysfunction or toxicity, more particularly against Aβ-induced cell death, Aβ-induced axonal degeneration, Aβ-induced electrophysiological dysfunction, and/or Aβ-induced synapse loss.

According to yet another of its aspects, the invention is directed to a method for preventing and/or treating diseases and/or injuries in which Caspase-2 activity is implicated, comprising at least a step of administering to an individual in need thereof at least an effective amount of at least one compound in accordance with the invention, in which $R_2$ is as above defined.

According to another of its aspects, the present invention relates to a pharmaceutical composition comprising at least one compound according to the invention in which $R_2$ is as above defined, and at least one pharmaceutically acceptable excipient.

The pharmaceutical compositions of the invention may contain more particularly an effective dose of at least one compound according to the invention in which $R_2$ is as above defined.

An "effective dose" means an amount sufficient to induce a positive modification in the condition or injury to be regulated or treated, but low enough to avoid serious side effects. An effective dose may vary with the pharmaceutical effect to obtain or with the particular condition being treated, the age and physical condition of the end user, the severity of the condition or injury being treated/prevented, the duration of the treatment, the nature of other treatments, the specific compound or composition employed, the route of administration, and like factors.

A compound of formula (I) according to the invention in which $R_2$ is as above defined may be administered in an effective dose by any of the accepted modes of administration in the art.

In one embodiment, this compound may be used in a composition intended to be administrated by oral, nasal, sublingual, ophthalmic, topical, rectal, vaginal, urethral or parenteral injection route.

The route of administration and the galenic formulation will be adapted by one skilled in the art pursuant to the desired pharmaceutical effect.

One of ordinary skill in the art of therapeutic formulations will be able, without undue experimentation and in reliance upon personal knowledge, to ascertain a therapeutically effective dose of a compound of the invention for a given indication.

A pharmaceutical composition of the invention may be formulated with any known suitable pharmaceutically acceptable excipients according to the dose, the galenic form, the route of administration and the likes.

As used herein, "pharmaceutically acceptable excipients" include any and all solvents, dispersion media, coatings, antibacterial and antifungal agents, isotonic and absorption delaying agents and the like. Except insofar as any conventional excipient is incompatible with the active compounds, its use in a medicament or pharmaceutical composition of the invention is contemplated.

A medicament or pharmaceutical composition of the invention may be in the form of tablets, pills, powders, lozenges, sachets, cachets, elixirs, suspensions, emulsions, solutions, syrups, aerosols, sprays, ointments, gels, creams, sticks, lotions, pastes, soft and hard gelatine capsules, suppositories, sterile injectable solutions, sterile packages powders and the like.

According to one embodiment, a pharmaceutical composition of the invention may be intended to be administered separately, sequentially or simultaneously with an agent useful for the prevention and/or the treatment of a disease condition, in particular Alzheimer's disease, said agent being different from the compound of formula (I) of the invention.

b) Activity-Based Probe

The compounds of the present invention and more particularly the compounds for which the $R_2$ radical is selected from:

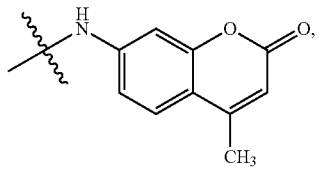

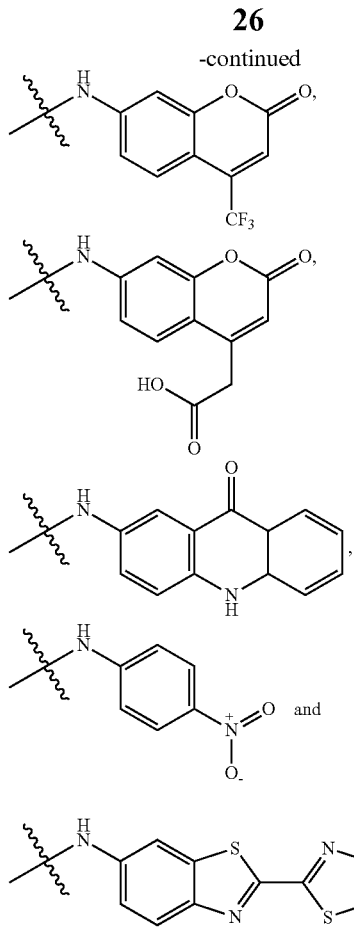

may be used as activity-based probe to selectively detect Caspase-2 activity.

Thus, according to one of its aspects, the present invention relates to the use of a compound according to the invention in which $R_2$ is as above defined, as activity-based probe (ABP) to selectively detect Caspase-2 activity.

The present invention will be better understood by referring to the following examples which are provided for illustrative purpose only and should not be interpreted as limiting in any manner the instant invention.

EXAMPLES

Example 1: Preparation of the Compound 2 According to the Invention

The synthesis of compounds according to the invention is inspired by the process of preparation of the compound TRP601 represented below:

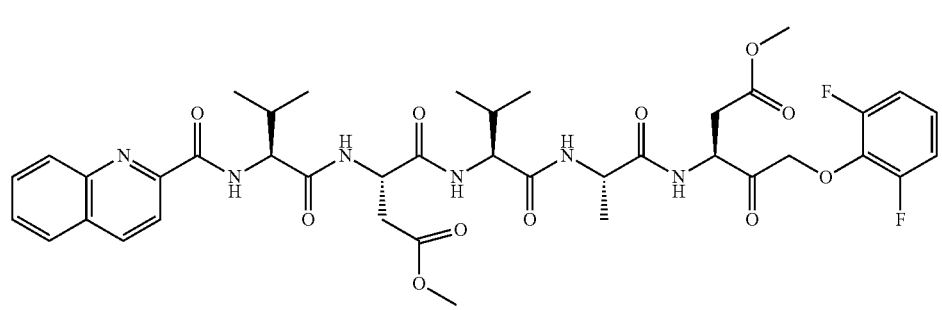

TRP601

The synthesis of TRP601 is described in D. Chauvier et al., Cell Death and Disease (2011) 2, e203.

For example, Compound 2 of the present invention differs from TRP601 in that:

$P_1$ and $P_4$ are represented by

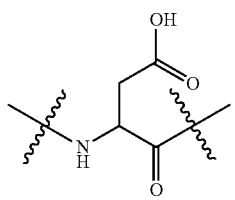 [SMILES: *NC(CC(=O)O)C(*)=O]

instead of

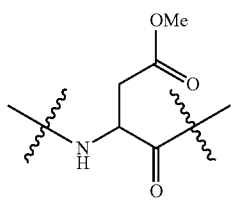 [SMILES: *NC(CC(=O)OC)C(*)=O]

in TRP601; and

The proline like residue

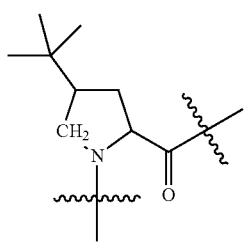 [SMILES: *C(=O)C1CC(C(C)(C)C)CN1*]

is used instead of

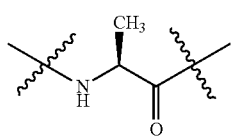 [SMILES: *N[C@@H](C)C(*)=O]

in TRP601.

The compound 2 has thus been obtained by reproducing the steps disclosed in the above-mentioned article to lead to TRP601 except that:

the precursor

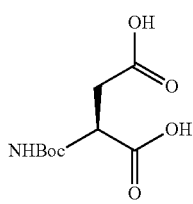

has been used instead of

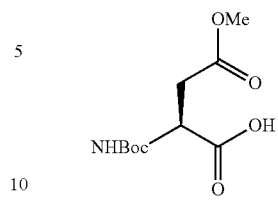

to introduce the $P_1$ and $P_4$ radicals; and
the precursor

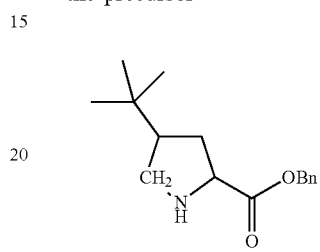

has been used instead of

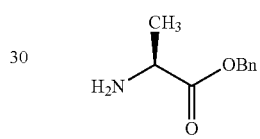

to introduce the proline like radical with either the configuration (R or S) of the asymmetric carbon atom of pyrrolidine ring linked to

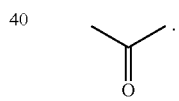

The precursor of $P_1$ and $P_4$ has been prepared starting from the commercially available (S)-aspartic acid in which the amine function has been protected by a Boc group according to a well-known protocol for the skilled artisan.

The precursor of proline has been obtained according to was obtained as described by Maillard et al., in Bioorganic & Medicinal Chemistry 19 (2011):5833-5851.

The other building blocks of the compound 2 have been introduced in the same manner as for TRP601 in the above-mentioned publications, i.e. with the same reagents, in the same conditions and with the same quantities.

Compound 2 has thus been obtained with a yield of more than 90% and characterized by HPLC, with either the configuration (R or 5) of the asymmetric carbon atom of pyrrolidine ring linked to

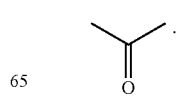

Example 2: Caspase-2 and Caspase-3 Inhibition Assays (In Vitro) for Irreversible Inhibitors The inhibitory efficiency of compounds of the invention which are irreversible inhibitors of Caspase-2 and Caspase-3 can be evaluated by using the below explained protocol. Compound 2, as well as compounds 4, 5, 6 are irreversible inhibitor and has been evaluated accordingly.

The efficiency of the comparative compound Δ2Me-TRP601, that is an already known group II Caspase inhibitor (inhibitor of Caspase-2, Caspase-3 and Caspase-7), has been assessed by a similar protocol described in Chauvier et al., 2011 Cell Death Dis 2011, 2:e203.

These tested compounds are represented below:

$k_{inact}$ is the maximal inactivation rate constant, and $K_I$ is the dissociation constant according to:

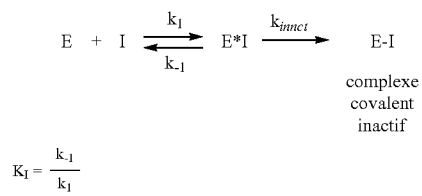

$$K_I = \frac{k_{-1}}{k_1}$$

that reflects the inhibitor affinity regarding an enzyme.

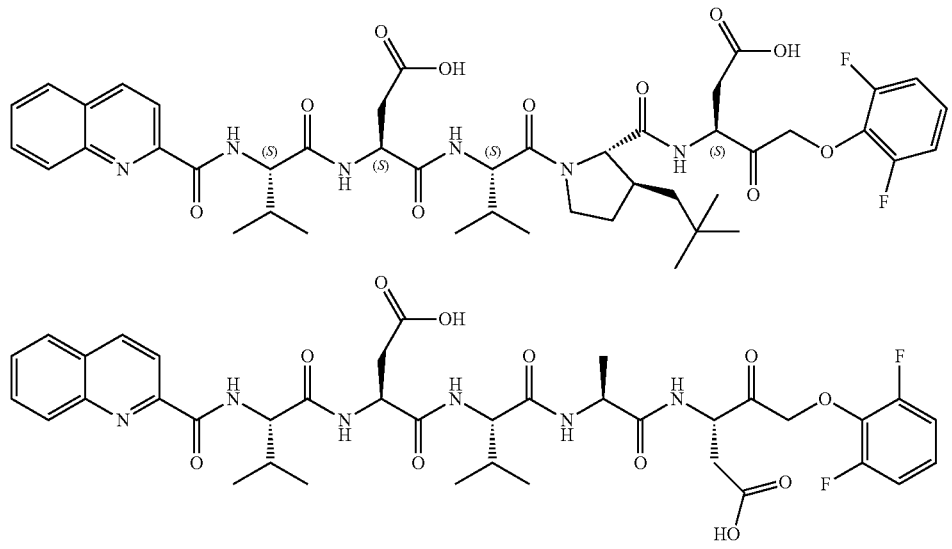

Compound 2

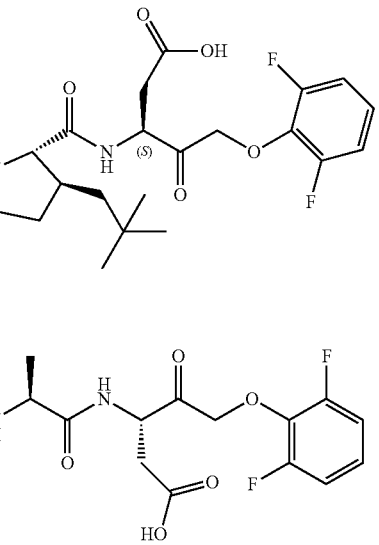

Δ2Me-TRP601 (comparative compound)

In this example, the Caspase-2 and Caspase-3 are human recombinant active enzymes that are respectively provided by Enzo Life® (ALX-201-057-U100) and R&D Systems® (707-C3-010/CF).

Caspase-2 is used at a final concentration of 0.1 nM in a "Caspase-2 buffer" containing 20 mM HEPES (pH 7.4), 5 mM DTT, 2 mM EDTA, 0.1% CHAPS and 800 mM succinate. Caspase-3 is used at a final concentration of 0.5 nM in a "Caspase-3 buffer" containing 20 mM HEPES (pH 7.4), 0.1% CHAPS, 5 mM DTT, and 2 mM EDTA.

The peptide substrates used for the enzymatic activity measurements are Ac-DEVD-AMC and Ac-VDVAD-AMC commercialized by EnzoLife® (respectively referenced ALX-260-031-M005 and ALX-260-060-M005). They are fluorogenic due to the presence of their AMC (7-amino-4-methylcoumarin) end group. The releasing of AMC enables to follow the enzymatic activity in fluorescence unit RFU over time in a 96-wells microplate.

The fluorescence values are measured at 37° C. with a spectrofluorometer with a microplate reader BMG FLUOstar OPTIMA. This apparatus is driven by the software Biolise® and is equipped with thermoelectric cooling device by Peltier effect. The mathematical analyses of the experimental data are done with the software Kaleidagraph®.

The inhibitory properties of the tested compounds are evaluated by the determination of the $k_{inact}/K_I$ ratio regarding either Caspase-2 or Caspase-3 wherein:

Accordingly, the higher the ratio, the more efficient the inhibitor.

Said ratio is measured according to the continuous method (Allison R D. Curr Protoc Protein Sci. 2001 May; Chapter 3:Unit 3.5.; Chauvier et al., 2011 Cell Death Dis 2:e203; Tan et al., J Med Chem 2015, 58:598-312).

Briefly, Caspases activities were determined by monitoring the hydrolysis of fluorogenic substrates ($\lambda_{exc}$=355 nm, $\lambda_{em}$=460 nm) as a function of time, in the presence of untreated Caspases (control) or Caspases that had been incubated with a test compound, for 30 min minimum at 37° C. using a BMG Fluostar microplate reader (black 96-well microplates) and the initial velocity ($V_0$) was determined from the linear portion of the progress curve.

Substrates and compounds were previously dissolved in DMSO at 10 mM, with the final solvent concentration kept at lower 4% (v/v). $V_0$, relative velocities, $K_M$ and $IC_{50}$ were determined from experimental data using Mars data Analysis 2.0 and Kaleidagraph softwares.

For irreversible inhibitors as compound 2, inactivation can be represented by the minimum kinetic scheme, where E and I are the free forms of enzyme and inhibitor, E*I a kinetic chimera of the Michaelis complex and E-I the covalent complex or inactivated enzyme.

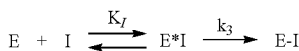

Inhibitor binding affinity (dissociation constant, $K_I$) and first-order rate constant ($k_3$) parameters were determined for Caspase-2 and Caspase-3 using the progress curve method. The ratio $k_3/K_I$ was obtained by fitting the experimental data to the equations (F.U., fluorescence unit):

$$F.U. = \int_0^t v_i dt + F.U._{\cdot 0}\frac{-v_0 \times e^{-\pi*t}}{\pi} + F.U._{\cdot 0}$$

with $\pi = \dfrac{k_i \times [I]'}{K_I + [I]}$ and $$[I]' = \frac{[I]}{1 + [S]/K_m}$$

Linear and nonlinear regression fits of the experimental data to the equations were performed with Kaleidagraph Software.

Determination of the $k_{inact}/K_I$ Ratio for the Caspase-2 and Caspase-3 Activity A continuous method of determination of the $k_{inact}/K_I$ ratio was used for evaluating the inhibitory activity of the tested compounds against Caspase-2 and Caspase-3.

The reaction mixture is prepared by letting the enzyme and the buffer incubate at 37° C.

The tested inhibitory compounds are prepared at different concentrations (¼ IC$_{50}$; ½ IC$_{50}$; IC$_{50}$; 2 IC$_{50}$; 4 IC$_{50}$) and put in the microplate.

Then the reaction mixture comprising the enzyme, the buffer and the substrate is rapidly added in the wells.

The activities of the enzyme are measured between 45 and 60 minutes.

The RFU (Relative Fluorescence Units)=f(times) curves are traced for each concentration of tested molecule according to the following equation:

$$((((-V_0)*(\exp(-k_{obs}*m0)))+V_0)/k_{obs}*)+RFU_0$$

in which:

$V_0$ corresponds to the initial rate (RFU·s$^{-1}$) in the concentration of 0 of the tested inhibitory compound;

$k_{obs}$ is the inactivation rate constant;

$RFU_0$ is the fluorescence value at t=0 min; and m0 is the variable i.e. the inhibitor concentration.

Adjusting the curve $f([I])=k_{obs}$ in an hyperbole using the Kaleigagraph software is then done in order to obtain the $k_{inact}/K_I$ ratio on the basis of the following equation:

$$K_{obs} = k_{intact} \times [I]/(K_I \times [I])$$

For compounds, 2, 3, 5 and 6 and Δ2Me-TRP601, the comparison of so-obtained $k_{inact}/K_I$ ratios regarding caspase 2 and 3 allow to appreciate their selectivity.

TABLE 1

| Inhibitor | Selectivity for Caspase 2 |
|---|---|
| Compound 2 | yes |
| Compound 4 | yes |
| Compound 5 | yes |
| Compound 6 | yes |
| Δ2Me-TRP-601 (comparative compound) | no |

Tested compounds are found efficient to inhibit Caspase-2.

However, compound 2 reacts totally differently than Δ2Me-TRP-601 with respect to Caspase-3 (see Table 2 below).

TABLE 2

| | $k_3/K_I$ (M$^{-1}$·s$^{-1}$) | | |
|---|---|---|---|
| | Casp2 | Casp3 | Selectivity ratio (C2/C3) |
| Δ2Me-TRP-601 | 1 586 020 | 1 613 405 | 0.98 |
| Compound 2 enantiomer a | 1 894 076 | 2 625 | 721 |
| Compound 2 enantiomer b | 1 720 | ND | +++ |

ND: no detectable inhibitory activity.
+++: as no inhibitory activity is detectable toward casp3, selectivity is very important (>>1000).

Indeed, compound 2 is much more efficient to inactivate Caspase-2 than to inactivate Caspase-3 whereas Δ2Me-TRP-601 does not exhibit this selectivity.

As a conclusion, compound 2 is not only efficient to inhibit Caspase-2, but is also selective regarding Caspase-2 with respect to Caspase-3. Interestingly, it is noteworthy that very different level of inhibition of caspase 2 are noticed depending on the configuration (R or S) of the asymmetric carbon atom of pyrrolidine ring linked to

Then compounds of the invention provide either moderate or strong, but highly specific, inhibitors of caspase 2 (Table 2) which is of particular interest.

Example 3: Caspase-2 and Caspase-3 Activity Detection

To determine the efficiency of a substrate with respect to an individual caspase we measure the ratio $k_{cat}/K_M$ which accounts for the catalytic efficiency, where $k_{cat}$ (s$^{-1}$) is the catalytic constant or number of substrate molecules converted to product per time unit by each active site when the enzyme is saturated and $K_M$ is the Michaelis-Menten constant which accounts for the enzyme-substrate affinity, it represents the substrate concentration for $v=V_{max}/2$.

Caspase-2 (or caspase-3) is incubated with the inhibitor or buffer alone, adapted to the enzyme and to the Michaelis-Menten complex, for 30 min at 37° C. The reaction is triggered, in a total volume of 100 when the buffer-substrate mixture is added; the enzymatic activity is then measured over 20 minutes. The release of the fluorogenic AMC group is detected using the following wavelengths: λexc=360 nm and λem=460 nm.

TABLE 3

| Enzymes | AMC Substrates | $k_{cat}/K_M$ (index) |
|---|---|---|
| Casp-2 (0.1 nM) (62 kDa) | Ac-VDVAD-↓-AMC (25 μM) | ++++ |

TABLE 3-continued

| Enzymes | AMC Substrates | $k_{cat}/K_M$ (index) |
|---|---|---|
| Caspase-3 (0.5 nM) (60 kDa) | Ac-VDVAD-↓-AMC (10 μM) | ++++ |
| Casp-2 (0.1 nM) (62 kDa) | Compound 1 (25 μM) | ++++ |
| Caspase-3 (0.5 nM) (60 kDa) | Compound 1 (10 μM) | +/− |

↓: cleavage site of the enzyme

The enzymatic activity is characterized by the initial velocity values (Vi) which are defined from equation 1 (eq.1), where $V_{max}$ is the rate at which the enzyme is saturated with substrate, [S] is the substrate concentration. The initial velocity, expressed here in RFU·min$^{-1}$, is obtained experimentally from the slope value on the linear portion of the representation: f (time)=RFU, a value calculated directly by the Biolise® software.

$$Vi = V\max \times [S]/(Km+[S]) \quad (eq.1)$$

The initial velocity obtained for the control (V0) is considered to be 100% of the enzymatic activity. An inhibition is characterized by an activity, after treatment with the inhibitor, of less than 100%. The percentage of inhibition is calculated from equation 2 (eq. 2), where V0 is the initial rate of the negative control, Vi is the initial rate in the presence of the inhibitor.

$$\% \text{ Inhibition} = (1-(V0/Vi)) \times 100 \quad (eq. 2)$$

Example 4: Caspase-2 and Caspase-3 Inhibition Assays (In Vitro) for Reversible Inhibitors The inhibitory efficiency of compounds of the invention which are reversible inhibitors of Caspase-2 and Caspase-3 can be evaluated by using the below explained protocol. Compound 3 is a reversible inhibitor and has been evaluated accordingly.

A preliminary step in the characterization of an inhibitor is the determination of its IC50. The IC50 is the necessary concentration of an inhibitor to decrease the enzyme activity by 50% of its maximum and uninhibited value.

The compound, at different concentrations, is incubated with the enzyme and buffer for 30 minutes at 37° C. to allow formation of the Enzyme-Inhibitor complex. The reaction is initiated by addition of buffer and substrate, and then activity is measured over 15 minutes for the determination of initial velocities. The inhibitory effect of the analyzed compound (in %) as a function of its concentration generally follows equation 3 (eq. 3) which translates a hyperbola. The equation is entered in the Kaleidagraph software, for the adjustment of the curve f ([I])=% Inhibition, where [I] is the inhibitor concentration, the IC50 is then obtained.

$$\% \text{ Inhibition} = 100 \times [I]/(IC50+[I]) \quad (eq. 3)$$

Evaluation of Reversible Inhibitors

The reversibility of the inhibition is analyzed by the dilution method for Ac-VDVAD-CHO, Ac-DEVD-CHO and compound 3. The enzyme and the inhibitor (or DMSO as control) are incubated for 30 minutes at 37° C. The complex thus formed is diluted to 100$^{th}$ in the buffer/substrate mixture and then the activity measurement is started over 20 minutes. The initial rate obtained for the DMSO represents the 100% activity and will serve as a reference for the quantification of the residual activity of the enzyme in the presence of the inhibitor.

In order to characterize the reversible inhibitors, the dissociation constant Ki is determined. It gives an account of the affinity of the inhibitor for the enzyme. For this purpose, the inhibitor is competed with the substrate with respect to the active site of the enzyme. If, after dilution, the activity is restored to more than 50%, the inhibitor is said to be "reversible".

The inhibitor is incubated with the Caspase-buffer mixture for 30 minutes at 37° C. at different concentrations (¼ IC$_{50}$, ½ IC$_{50}$, IC$_{50}$, 2 IC$_{50}$, 4 IC$_{50}$). The reaction is started over 20 minutes upon addition of the buffer-substrate mixture.

Initial velocity values in RFU·min$^{-1}$ are reduced to Specific Activity (SA) values (pmol/min/μg enzyme) from an AMC standard range (1 RFU→0.02 pmol).

The evolution of the ratio 1/SA as a function of 1/[S] makes it possible to obtain the so-called double-inverse graph of Lineweaver-Burk from equation 4 (eq.4) where $V_{max}$app and $K_M$app are the parameters which vary according to the type inhibition and as a function of inhibitor concentration. The intersection of the lines obtained for increasing inhibitor concentrations makes it possible to distinguish different types of inhibitors.

$$\frac{1}{V} = \frac{Kmapp}{V\max app} \times \frac{1}{[S]} + \frac{1}{V\max app} \quad (eq. 4)$$

A secondary graph, obtained from the values of the slopes of the Lineweaver-Burk plot as a function of the concentration of inhibitor, makes it possible to obtain the value of the Ki. Its value is given by the abscissa point at the origin.

The inhibitory powers of the compounds with respect to the Casp-2 and -3 are quantified by the determination of the IC$_{50}$. The results are presented in Table 3 (left). The IC$_{50}$ values place compound 3 at the head behind the reference compound Ac-VDVAD-CHO (IC$_{50}$=6.9 nM) in terms of efficacy on Casp-2. In addition to acting efficiently on Casp-2, compound 3 appears to be considerably less potent on Caspase-3 than Ac-VDVAD-CHO (IC$_{50}$=7.23 nM). Thus compound 3 is Casp2-selective.

The in-depth study of the inhibition mechanism was done as follows.

The initial velocity V0 is expressed from equation 8 (eq.8), where Vmax is the maximum reaction rate (reached when the enzyme is saturated with substrate), [S] the substrate concentration, $K_M$ is the Michaelis-Menten constant (substrate concentration corresponding to Vmax/2), Ki is the dissociation constant which accounts for the affinity of the inhibitor for the enzyme. The Ki allows to quantify the inhibitory power, the lower its value, the stronger the inhibitor.

$$\frac{1}{V0} = \frac{1}{V\max} + \frac{\left(1+\frac{[I]}{Ki}\right) \times Km}{V\max} \times \frac{1}{[S]} \quad (eq. 8)$$

The secondary track obtained from the Lineweaver-Burk graph data allowed the Ki values to be determined. The Ki values for the various inhibitors as well as the selectivity indexes are presented in Table 4 (right).

TABLE 4

| Inhibitors | IC$_{50}$ (nM) | | Ki (nM) | |
|---|---|---|---|---|
| | Casp-2 | Caspase-3 | Casp-2 | Caspase-3 |
| Ac-VDVAD-CHO | 6.9 ± 0.6 | 7.23 ± 0.66 | 6.31 | 7.68 |
| Ac-DEVD-CHO | 3907 ± 189 | 0.7 ± 0.03 | 3 222 | 0.159 |

TABLE 5

| Inhibitors | Selectivity Indexes (Ki$_{Casp3}$/Ki$_{Casp2}$) |
|---|---|
| Ac-VDVAD-CHO | 1.3 |
| Ac-DEVD-CHO | 62 × 10$^{-6}$ |
| Compound 3 | >>1000 |

The inhibitory efficiencies are represented by the IC$_{50}$ values for the Ac-DEVD-CHO and Ac-VDVAD-CHO reference inhibitors as well as for the P$_2$-variant Ac-VDVAD-CHO derivatives (Table 4). Quantification of the inhibition is given by the values of the Ki constants which account for the affinity of the inhibitor for the enzyme. A low value indicates a potent inhibitor on its target. The ratios of the constants allow to quantify the selectivity (Table 5), the higher the ratio, the more the inhibitor is selective of the Casp-2.

The Ki values confirm and supplement the information provided by the IC$_{50}$ data. Thus, compound 3 is an inhibitor that is still powerful on Casp-2 with a selectivity with respect to the latter markedly increased compared to Ac-VDVAD-CHO (Table 5).

Example 5: Protection Against Cellular Death Assay

In this example, the protective effect of the compound 2 of the invention against cellular death induced by vincristine (a vinca alkaloid) is tested using a well-known flow cytometry cell death assay based on propidium iodide staining.

a. Cellular Model

To evaluate the protecting effect of compounds 2 and 3, a Caspase-dependent cellular model is used.

Human HeLa cells are used in this model. HeLa cells (cervical cancer cell line) were obtained from American Type Cell Collection (ATCC), and were cultured in Dulbecco's Modified Eagle Medium (DMEM, High Glucose, GlutaMAX™, Pyruvate) (Gibco, Life technologies), supplemented with 10% FCS and antibiotics (Gibco, Life technologies).

Human HeLa cells are treated with a solution of Vincristine (Sigma Aldrich) (diluted in water at 5 mM). Vincristine works partly by binding to the Tubulin protein, stopping the cell from separating its chromosomes during the metaphase; the cell then undergoes apoptosis through a caspase-dependent process.

Propidium iodide (PI) (Sigma Aldrich) is used to evaluate plasma membrane permeabilisation, a sign of cell death.

b. Treatment and Marking Conditions 24 hours before pharmacological treatment, HeLa cells were plated into 24-well plates. Culture medium was then removed, cells were washed with PBS, and fresh medium containing compound 2 or 3 at different concentrations was added 1 hour before addition of vincristine. Cells were exposed or not (control), to 20 nM Vincristine for 48 hours.

The content of each well is collected is added to PBS and then centrifuged (900 rpm; 5 min).

The pellet obtained is put into 300 µL of a medium comprising propidium iodide and incubated (37° C., 5% CO$_2$) in the dark for 5 minutes and then subjected to flow cytometry analysis.

c. Cells Analysis

The cells are then analyzed by flow cytometry with an excitation of 561 nm.

Fluorescence-Activated Cell Sorting was performed using a FACSCalibur cytometer (Becton Dickinson, San Jose, Calif.). For each sample, data from 5,000 Cells were registered and analyzed with the CellQuest Pro software (Becton Dickinson). Analysis included FSC (Forward Scatter/relating to the cells'size) and SSC (Side Scatter/relating to the cells' granularity) parameters together with FL-1 and FL-3 channel.

TABLE 6

| Compostion | Index of cell death |
|---|---|
| Compound 2 and vincristine | ++ |
| Compound 3 and vincristine | ++ |
| Vincristine alone | ++++ |

The number of "+" is indicative of cell mortality measured in the assay. The higher the number of "+" represented, the higher the cell mortality measured in the assay.

The percentage of propidium iodide positive cells gives an estimation of cell death.

Control composition, which neither contains vincristine nor inhibitor, enables to estimate the quantity of cells that died naturally.

Composition containing vincristine but no inhibitor, provides the total number of dead cells that corresponds to the sum of naturally dead cells and of apoptotic cells induced by vincristine.

Inventors observe clearly that compound 2 and 3 protect the cells against apoptotic death induced by vincristine in a dose-dependent manner.

Example 6: Protection Against Abeta-Neurotoxicity a) Primary Neuronal Cultures

Hippocampus are micro-dissected from E16 embryos of C57B16/J wt mice (Rene Janvier, France) in cold Gey's Balanced Salt Solution (GBSS, Sigma) supplemented with 0.1% glucose (Life technologies).

Dissected structures are digested with papain (20 U/ML in DMEM, Sigma; St. Louis, Mo., USA) and mechanically dissociated in the presence of DNAse. Hippocampal cells are then rinsed and re-suspended in DMEM (Life Technologies, Inc., Gaithersburg, Md., USA) to a final density of 18 million cells/ml in Neurobasal (Life technologies) and Glutamax (0.1% LifeTechnologies) supplemented with B27 (1/50) and penicilline/sptreptomycine 1% (Gibco).

This cell suspension is then used to fill the reservoirs of microfluidic chambers, as described (Peyrin et al, 2011 Lab Chips 11(21):3663; Deleglise et al, 2014 Acta Neuropathologica Comm. 2: 145). Microfluidic chips are placed in plastic Petri dishes containing H20-EDTA to prevent evaporation and incubated at 37° C. in a humid 5% CO$_2$ atmosphere. The culture medium is renewed every seven days.

b) Preparation of Aβ Peptide Oligomers

Oligomeric form of Aβ$_{1-42}$ (Tocris Bioscience, MN, USA), is produced according to Stine W B et al (2003) in J Biol Chem 278, pp 11612-11622 and can be controlled by electron microscopy as in Deleglise B et al. in Acta Neuropathol Commun. 2014; 2: 145).

Briefly, Aβ$_{1-42}$ lyophilized peptides are solubilized at 1 mM in 1, 1, 1, 3, 3, 3,-hexafluoro-2-propanol (HFIP, Sigma Aldrich). After 30 min of incubation at RT, HFIP is evaporated for 12 h under chemical hood and peptides are dried for 1 h (with a Speed Vac at 4° C.). Then, 5 mM Aβ peptide stock solutions are obtained by resolubilization at in dimethylsulfoxide (DMSO, Sigma Aldrich). To obtain oligomers, Aβ peptide stock solution is diluted in cold phenol free DMEM-F12 medium (Life Technologies) to a final concentration of 100 µM. The solution is then incubated 24 h at 4° C. Soluble Aβ oligomer fraction is collected from the supernatant after a centrifugation step at 20 000 g (10 min; 4° C.), and stored at −80° C. until use.

c) Toxicity Assay

After 18 days of culture in micro fluidic chambers, hippocampal cells are pre-incubated for 1 h with compounds of the invention prior diluted in phenol free DMEM-F12 medium or in phenol free DMEM-F12 medium alone as a control solution. Cells are then intoxicated for 3 h to 6 h or 24 h with 10 or 100 nm of Aβ$_{1-42}$ oligomers (or with phenol free DMEM-F12 medium alone as a control solution). After the intoxication step, cells are fixed in 4% paraformaldehyde (PFA, Sigma; St. Louis, Mo., USA) for 20 min RT, and labelled as explained below to evaluate synapses status, cell death or axonal degeneration.

d) Immunofluorescence

Briefly, after the fixation step, cultures cells are washed twice with PBS+Azide 0.1% for 5 min and permeabilized for 10 min with 0.2% Triton X-100 and 0.1% BSA (Bovine Serum Albumin, Sigma) in PBS+Azide 0.1%. Saturation step is then realized by incubating cells during 30 min in PBS+Azide 0.1%+BSA1%. Primary antibodies are then added and the samples incubated at 4° C. overnight in PBS. Afterwards, samples are rinsed twice for 5 min with PBS+Azide 0.1% and further incubated with the corresponding secondary antibody together with phalloidin conjugated to Alexa Fluor 555 for 2 h RT. The chips were then rinsed twice with PBS+Azide 0.1%.

The following antibodies are used: rabbit polyclonal anti-MAP-2 (AB5622; 1/400, MILLIPORE), mouse monoclonal Anti-Bassoon SAP7F407; 1:400, Enzo LifeSciences). Species-specific secondary antibodies coupled to Alexa 350, 488 or 500 are used (1/500, Life Technologies, Inc., Gaithersburg, Md., USA). Phalloidin conjugated to Alexa Fluor 555 (1/500, EnzoLifeTechnologies) is used to stain F-actin.

e) Image Acquisition

Images are acquired with an Axio-observer Zl (Zeiss, Germany) fitted with a cooled CCD camera (CoolsnapHQ2, Ropert Scientific). The microscope is controlled with Metamorph and Micro-manager software. Images were analyzed using ImageJ software.

f) Results

In the Aβ intoxicated cells, but not pretreated with compounds of the invention, a marked decrease in anti-Bassoon labelling is noticed as soon as 6 h of intoxication when compared with non-intoxicated samples. This loss of dendritic spines in hippocampal neurons mice provides evidence of neurodegeneration due to Aβ synaptotoxicity and results in the marked decrease in synapse number (almost 50%, FIG. 1). Further, 24 hours post-Aβ treatment, axonal degeneration is noticed for hippocampal neurons which have been not pretreated with compounds of the invention. Compounds of the invention are found efficient in protecting hippocampal cells from Aβ-induced cell death, Aβ-induced axonal degeneration, Aβ-induced electrophysiological dysfunction, and/or Aβ-induced synapse loss (Table 7 and FIG. 1).

TABLE 7

| Composition | Protective effect against Aβ toxicity |
| --- | --- |
| Compound 2 | + |
| Compound 3 | + |
| Compound 4 | + |
| Compound 5 | + |
| Compound 6 | + |
| Aβ alone | − |

+: significant protection against a Aβ-induced cell death, Aβ-induced axonal degeneration, Aβ-induced electrophysiological dysfunction, and/or Aβ-induced synapse loss.

Those experiments provide evidences that compounds of the invention, which are able to modulate the activity of Caspase-2 (tables 1 and 5), are efficient to treat or prevent the occurrence of disorder associated with Aβ neurotoxicity.

Conclusion

Compounds of the invention are thus valuable compounds for the treatment of diseases associated with cell death or dysfunction mediated by Caspase 2 activity. More particularly, they are found to be efficient in treating neurodegenerative disorders as Alzheimer's disease (AD), Aβ synaptotoxicity being known to play an important in the pathophysiology of this disease. Furthermore, Caspase 2 is known in the art to mediate cleavage of tau which generates Δtau314, found implied in the cognitive decay in AD, thus making compounds of the invention valuable compounds for their use in treating or preventing diseases implying either tau and or Aβ toxicity.

The invention claimed is:

1. A compound of formula (I):

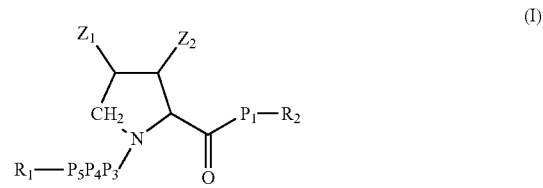

in which:
Z$_1$ and Z$_2$, identical or different are selected from a hydrogen atom, a (C$_1$-C$_6$)alkyl and a (C$_1$-C$_6$)alkoxy group;
P$_5$ is selected from the following amino acids residues or amino acid like structures:

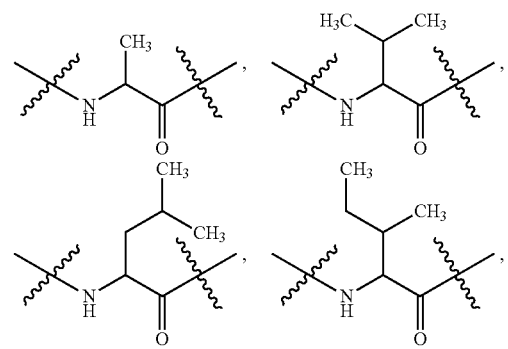

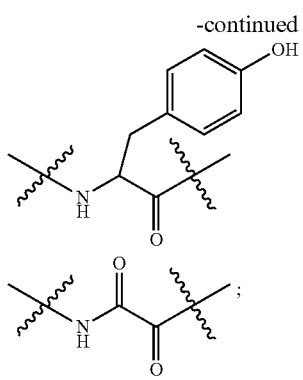
and
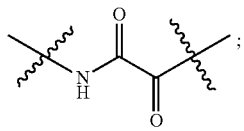;
P₁ and P₄, identical or different, are selected from the following amino acid like structures:
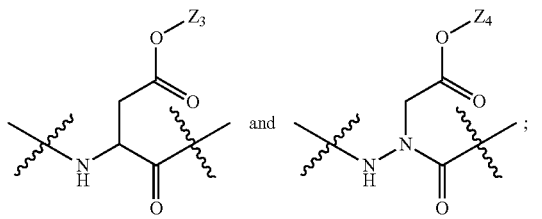
in which Z₃ and Z₄, identical or different, are selected from a hydrogen atom and a $(C_1\text{-}C_6)$alkyl group;
P₃ is selected from the following amino acid residues:
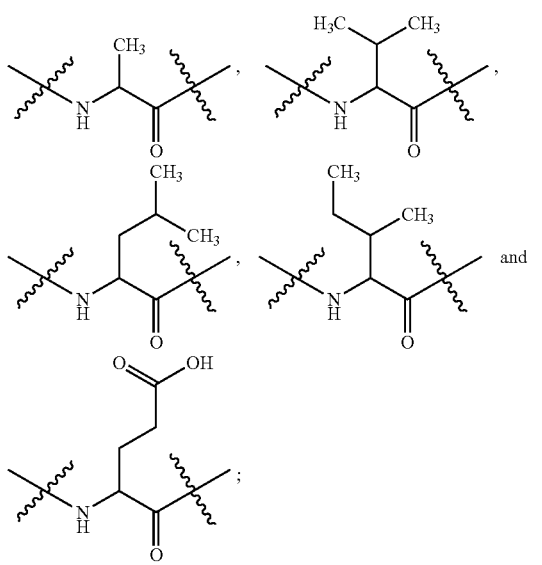
R₁ is selected from:
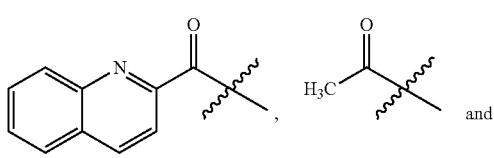
and
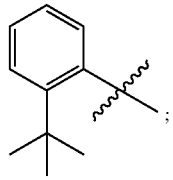;
and
R₂ is selected from:
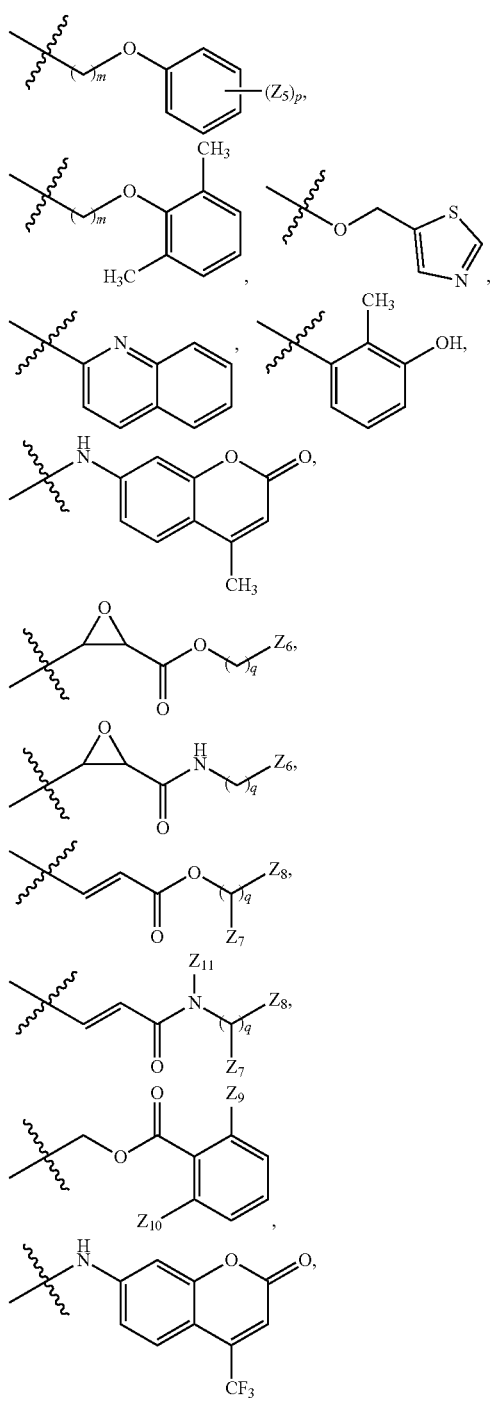

-continued

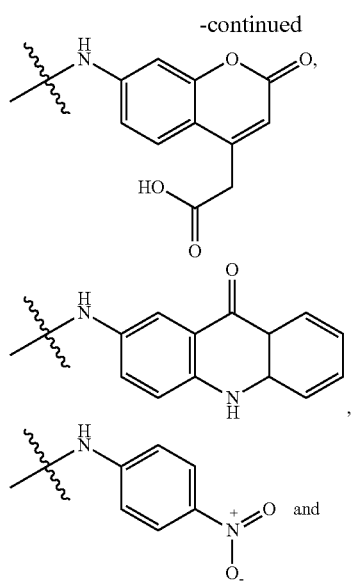

in which:
m is 0, 1 or 2;
p is 1, 2, 3 or 4;
$Z_5$ is a halogen atom;
q is 0 or 1;
$Z_6$ is selected from a $(C_1-C_6)$alkyl and a phenyl group, said phenyl group being optionally substituted by an amino group;
$Z_7$, $Z_8$ and $Z_{11}$, identical or different, are selected from a hydrogen atom, a $(C_1-C_4)$alkyl, a tetrahydroquinolynyl and a $-(CH_2)_i$-aryl group with i being 0, 1 or 2, said aryl group being optionally substituted by one, two, three, or four halogen atom(s) or one $(C_1-C_4)$ alkyl group; and
$Z_9$ and $Z_{10}$, identical or different, are selected from a halogen atom and a $(C_1-C_6)$alkyl group;
or its salt, racemic, enantiomeric or diastereoisomeric isomer form.

2. The compound according to claim 1 of formula (II):

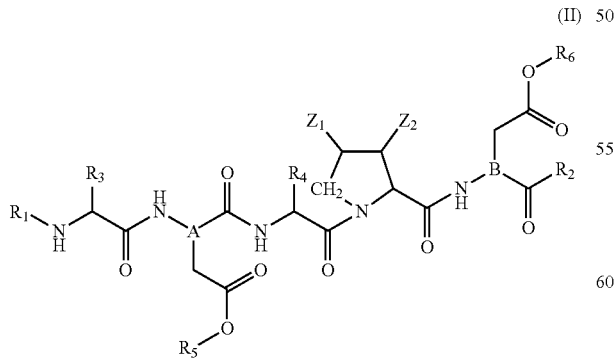

wherein:
$R_1$ and $R_2$ are as defined in the formula (I) according to claim 1;

$Z_1$ and $Z_2$ are as defined in the formula (I) according to claim 1;
$R_3$ is selected from a $-CH_3$, a $-CH(CH_3)_2$, a $-CH_2CH(CH_3)_2$ a $-CH(CH_3)CH_2CH_3$ and a 4-hydroxyphenyl group;
A and B, identical or different, are selected from a nitrogen atom and a $-CH-$ group;
$R_5$ and $R_6$, identical or different, are selected from a hydrogen atom and a $(C_1-C_6)$alkyl group; and
$R_4$ is selected from a $-CH_3$, a $-CH(CH_3)_2$, a $-CH_2CH(CH_3)_2$, a $-CH(CH_3)CH_2CH_3$ and a $-(CH_2)_2CO_2H$ group;
or its salt, racemic, enantiomeric or diastereoisomeric isomer form.

3. The compound of formula (II) according to claim 2, wherein at least one of A and B is a $-CH$ group.

4. The compound according to claim 1 of formula (III):

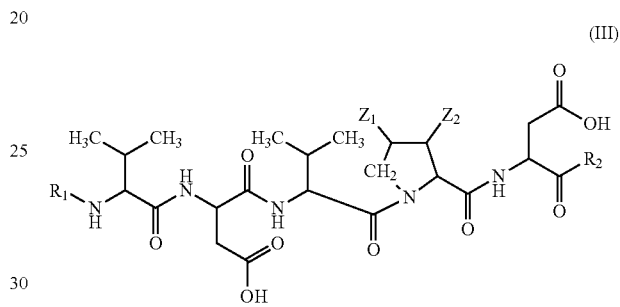

wherein $R_1$ and $R_2$ are as defined in the formula (I) according to claim 1;
or its salt, racemic, enantiomeric or diastereoisomeric isomer form.

5. The compound according to claim 1, wherein $R_1$ is:

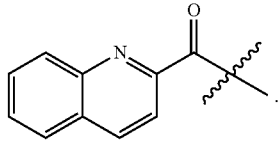 [SMILES: *C(=O)c1ccc2ccccc2n1]

6. The compound according to claim 1, wherein $R_2$ is selected from:

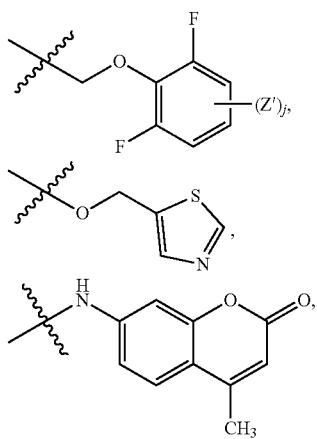

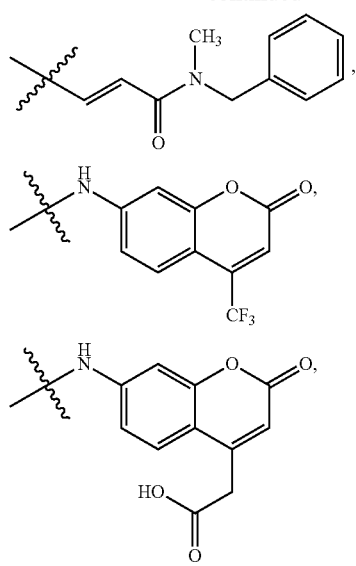
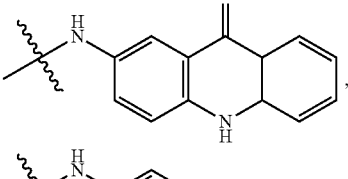
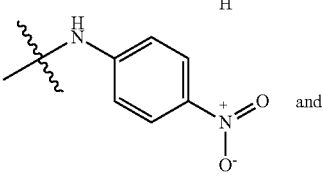
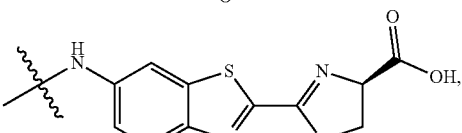
in which Z' is a fluorine atom and j is 0, 1 or 2.
7. The compound according to claim 1, having at least one asymmetric carbon atoms of (S) configuration.
8. A compound of formula (I), selected from:
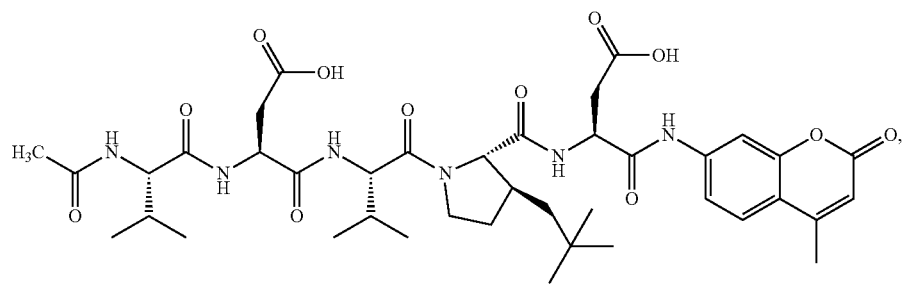
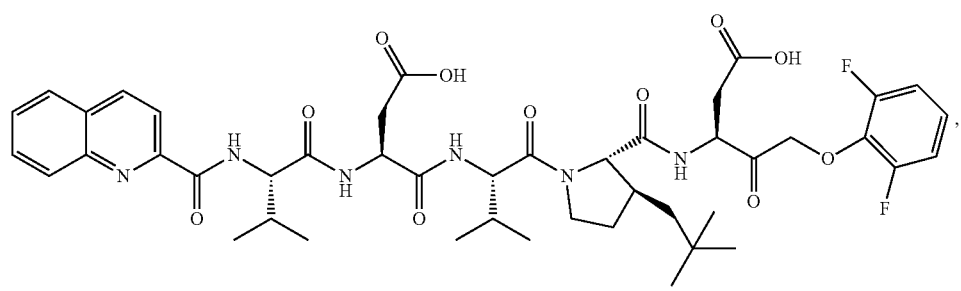
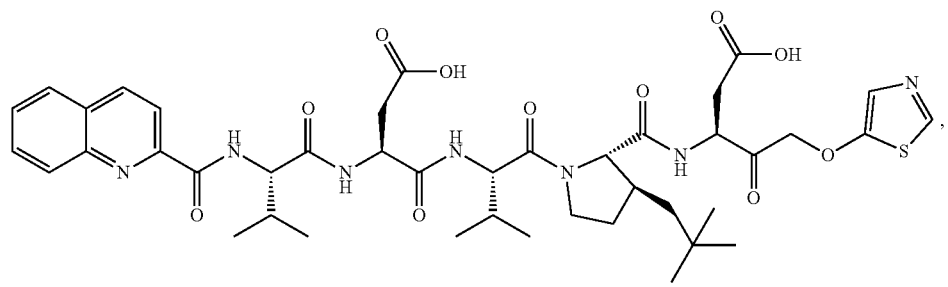

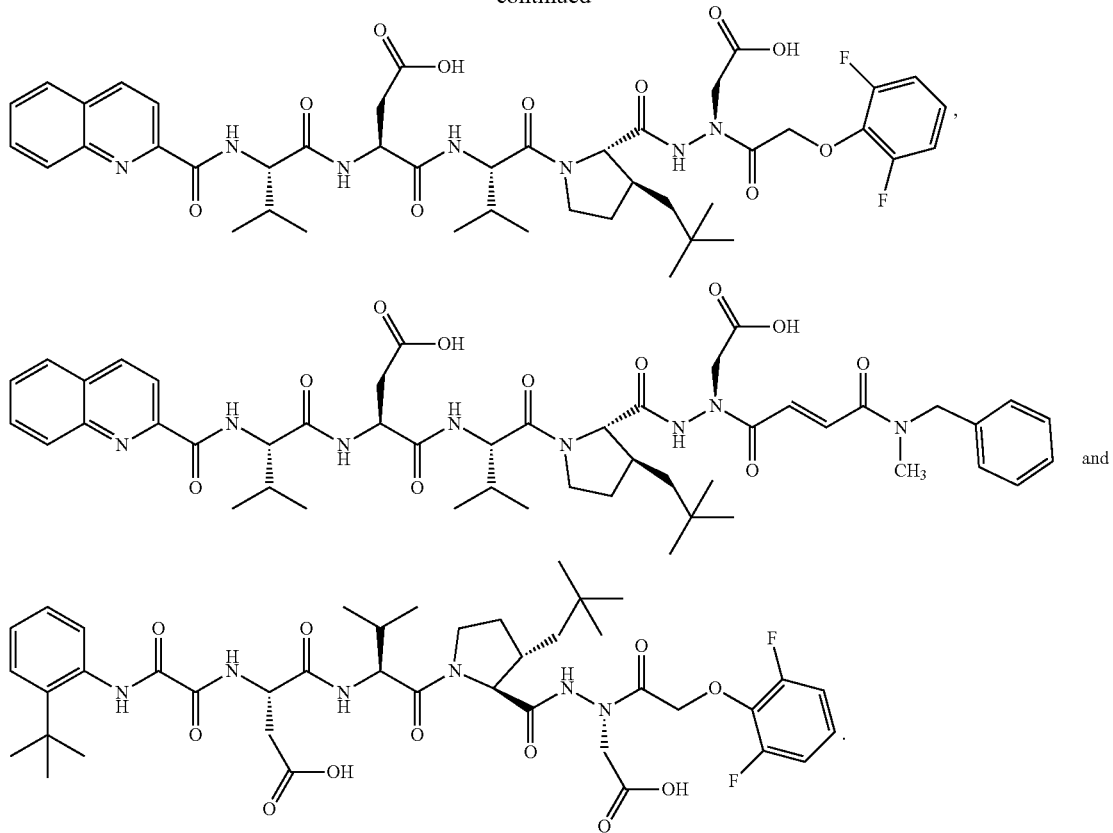
9. The compound according to claim 1, wherein the compound demonstrates activity as selective Caspase-2 inhibitor.
10. A pharmaceutical composition, comprising at least one compound according to claim 1 and at least one pharmaceutically acceptable excipient, wherein $R_2$ is selected from:
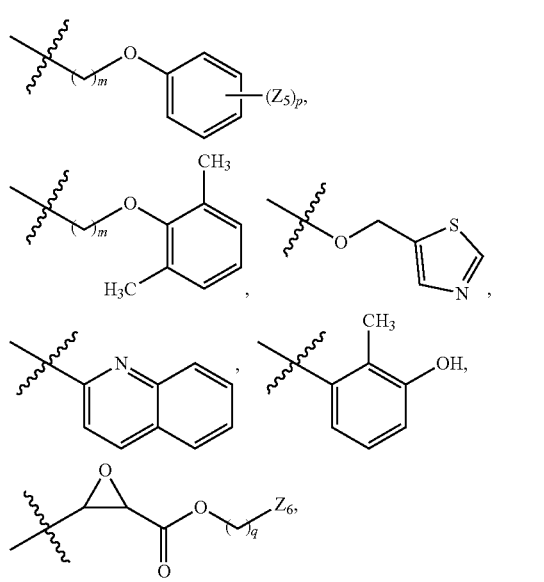
-continued
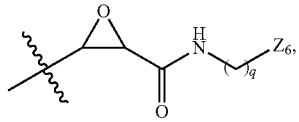
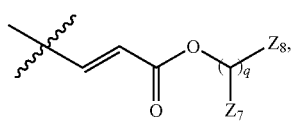
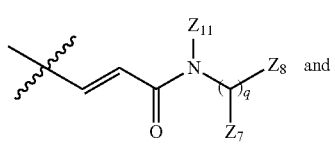 and
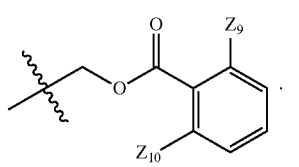

11. A method for selectively inhibiting caspase-2 activity in a subject in need thereof, comprising administering to the subject a compound of claim 1, wherein $R_2$ is selected from:

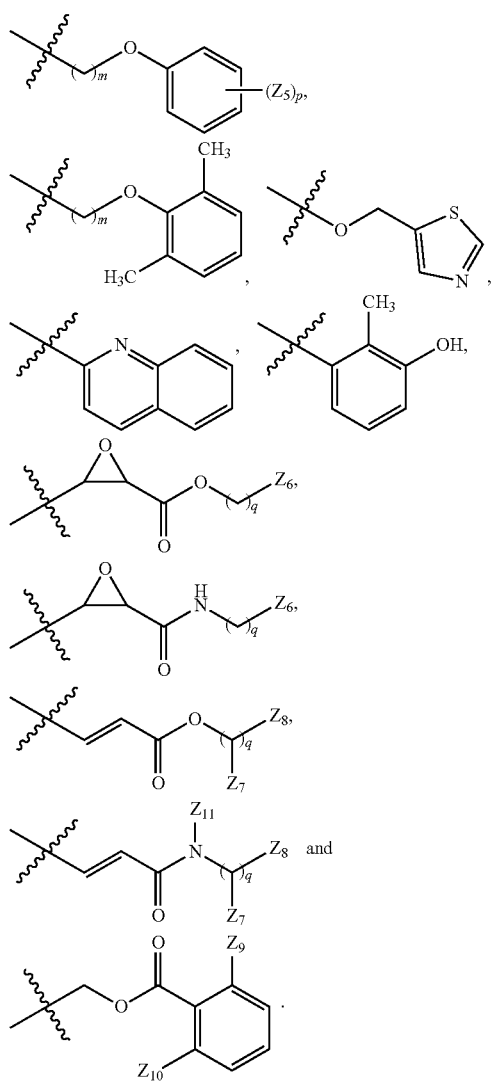

12. The method according to claim 11 for inhibiting caspase-2 mediated cell death in said subject.

13. The method according to claim 11 for protecting neuronal cells from Aβ-induced dysfunction or toxicity.

14. A method of selectively detecting Caspase-2 activity, comprising contacting a biological sample with the compound according to claim 1 as an activity-based probe, wherein $R_2$ is selected from:

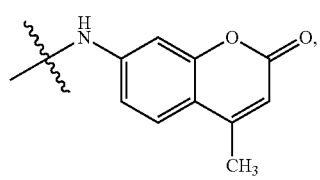

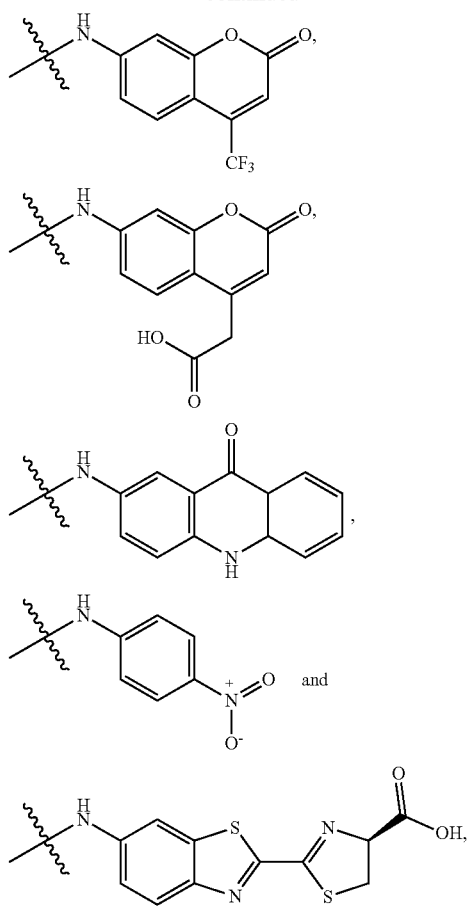

and detecting Caspase-2 activity.

15. The compound of formula (II) according to claim 3, wherein A and B are —CH groups.

16. The compound according to claim 1, wherein R2 is selected from:

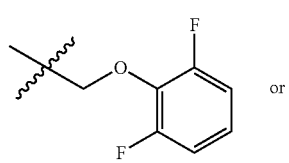

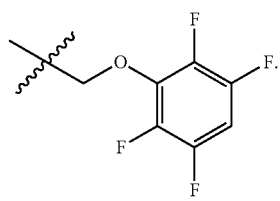

17. The compound according to claim 1, having at least three asymmetric carbon atoms of (S) configuration.

18. The compound according to claim 1, wherein all the asymmetric carbon atoms are of (S) configuration.

19. The compound of formula (I) selected from among:
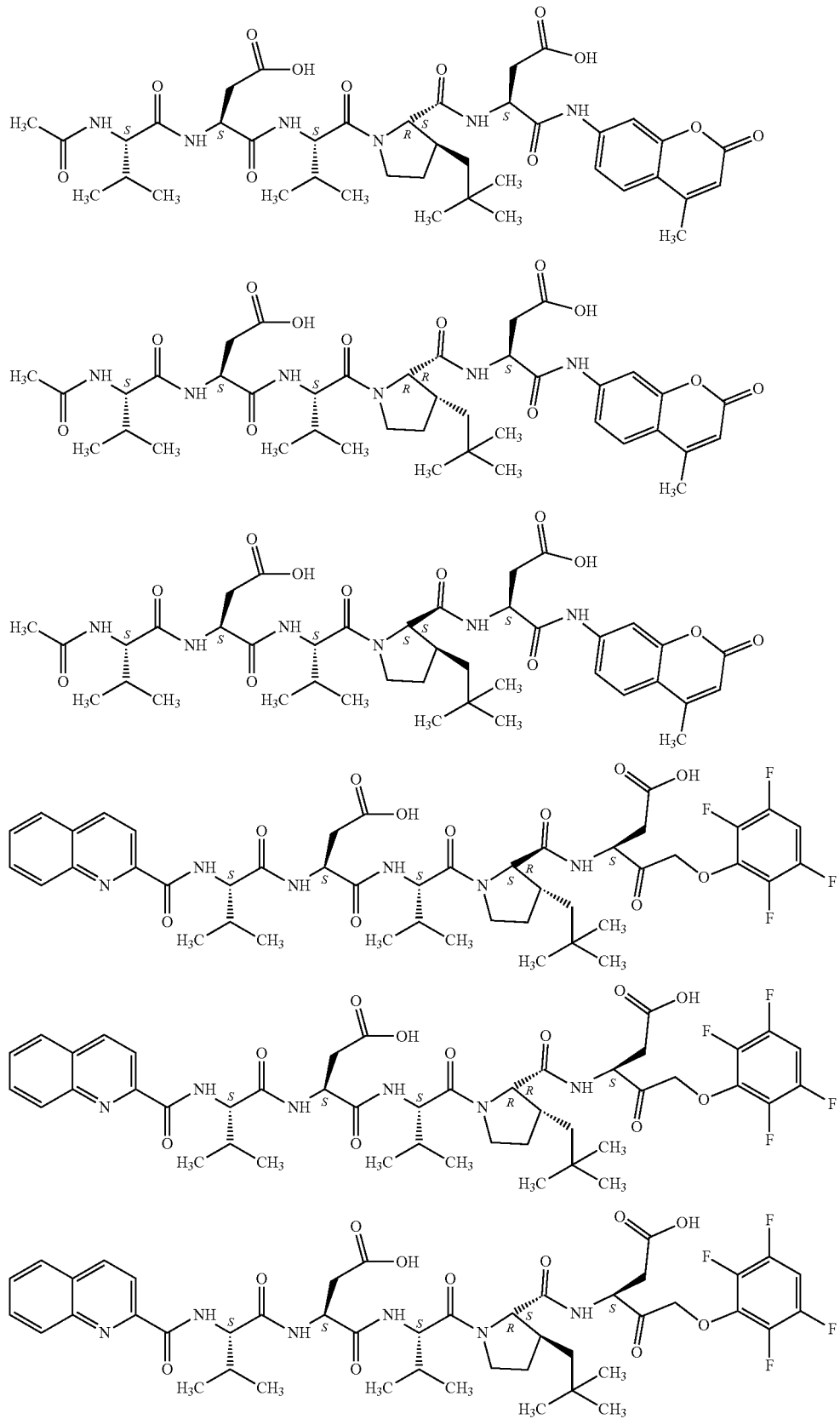

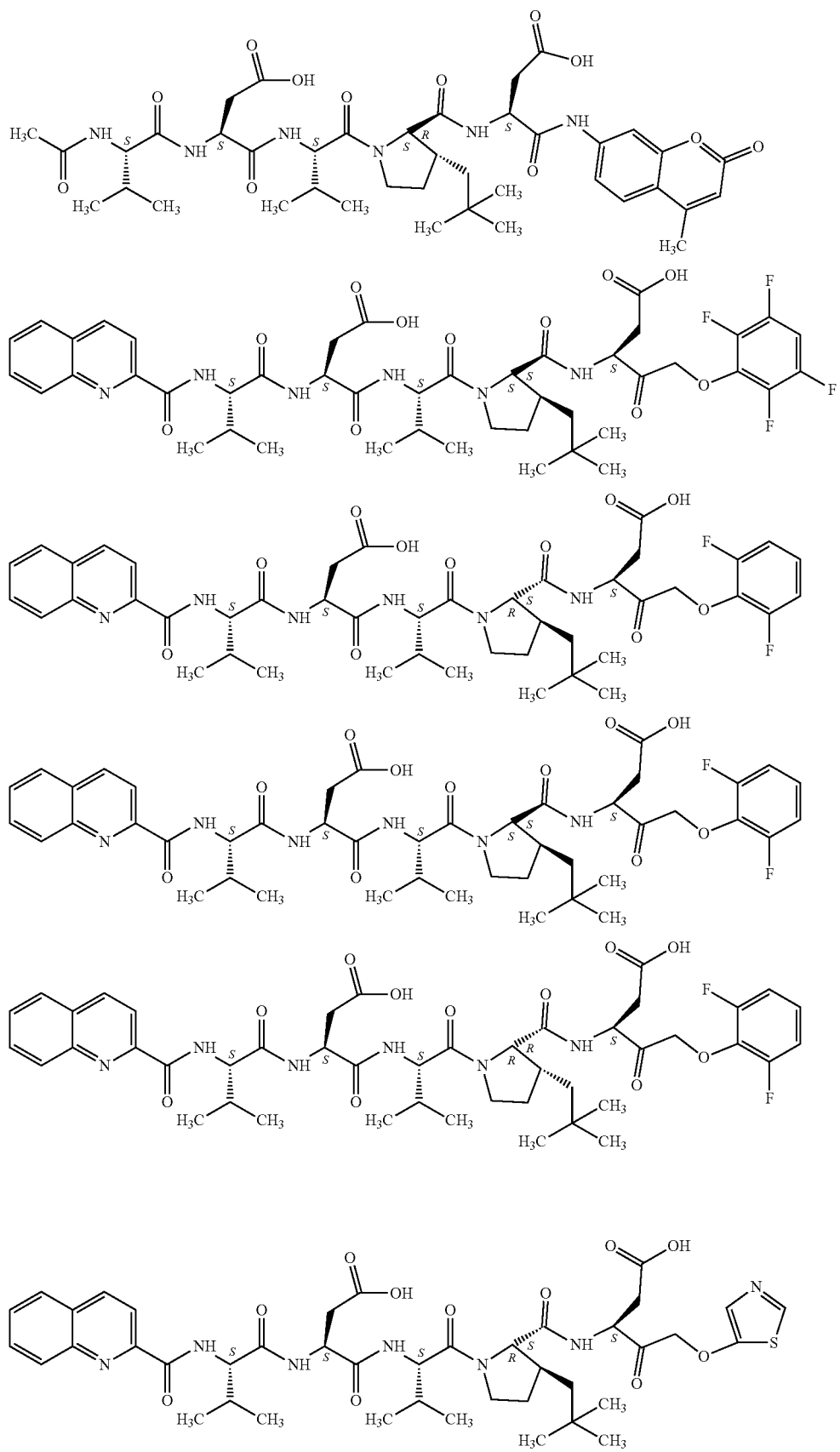

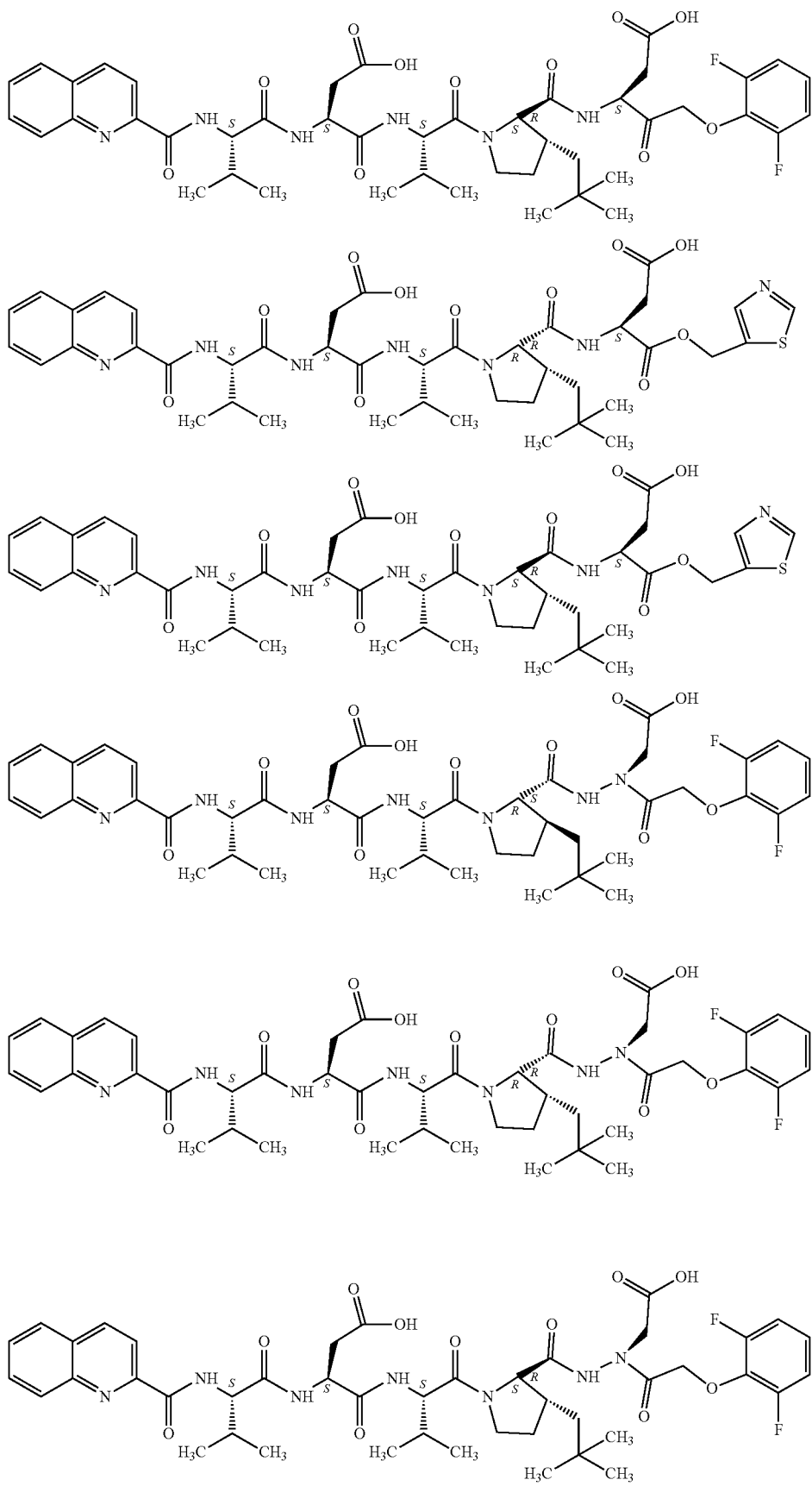

-continued
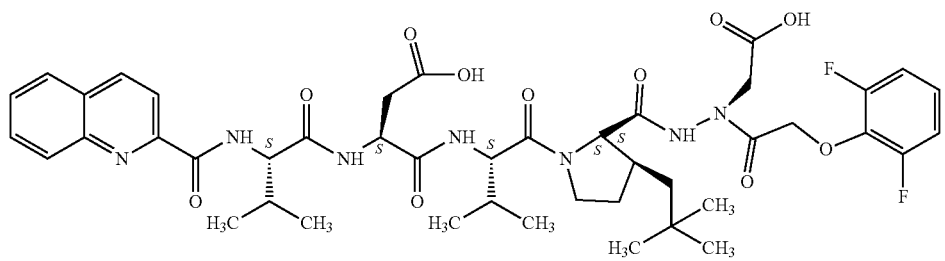
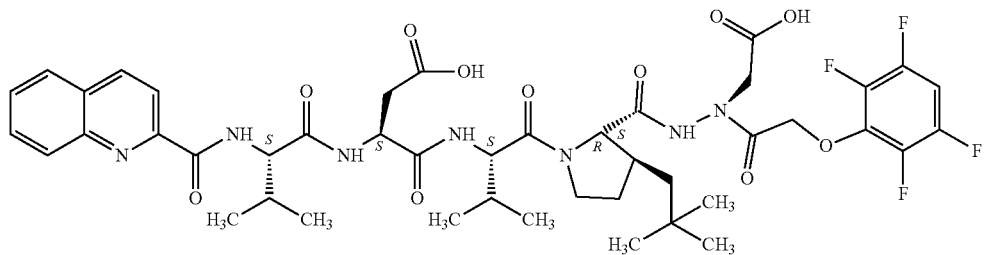
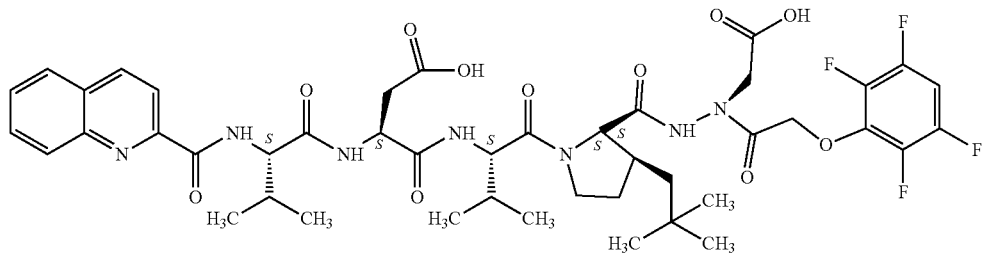
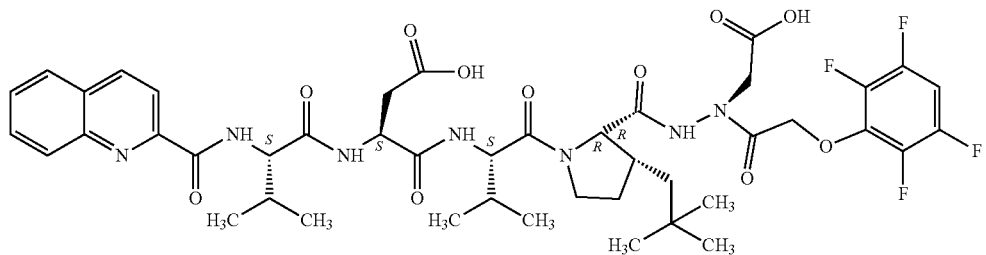
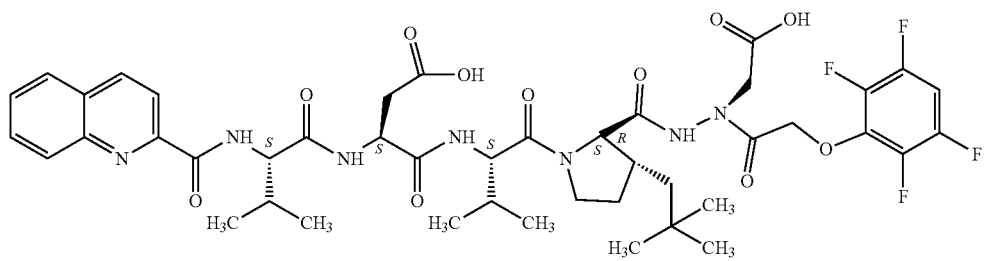
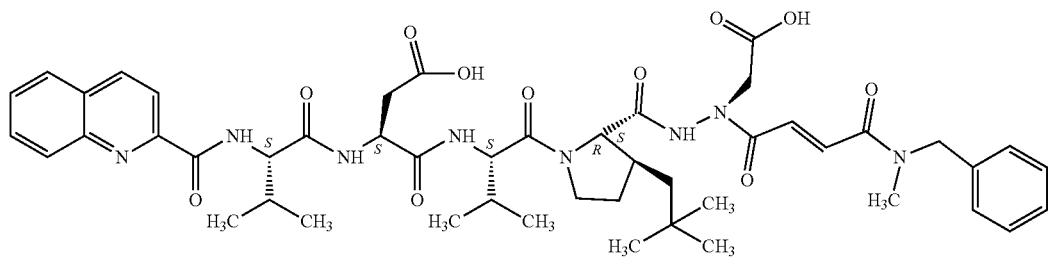

-continued
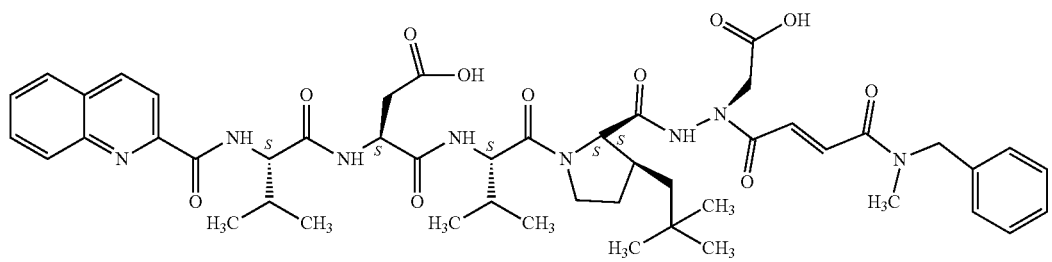
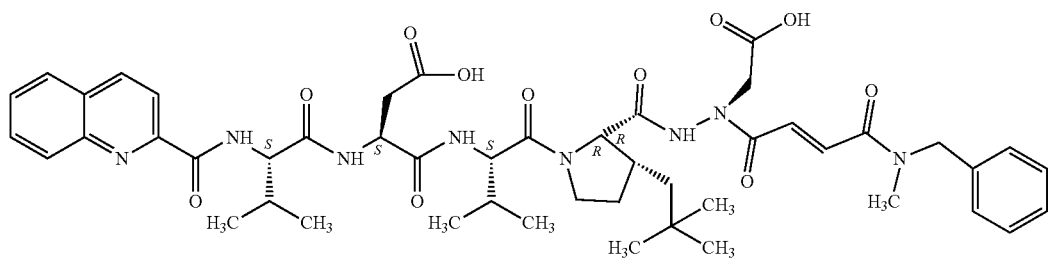
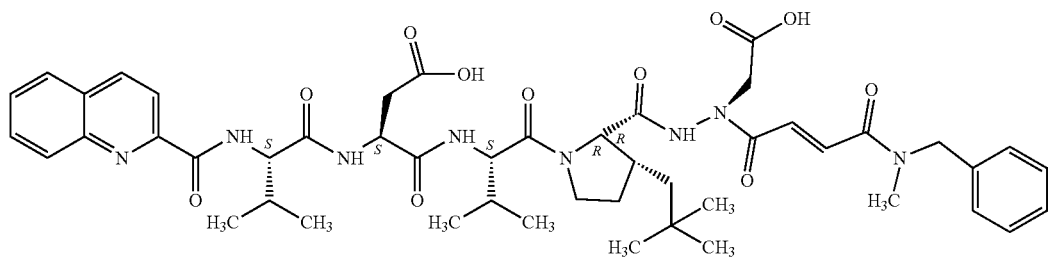
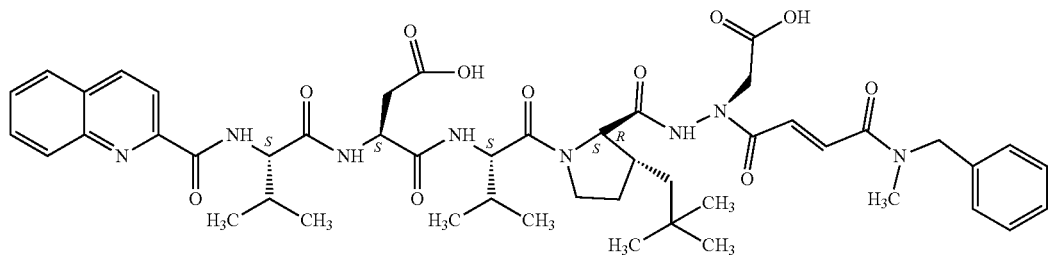
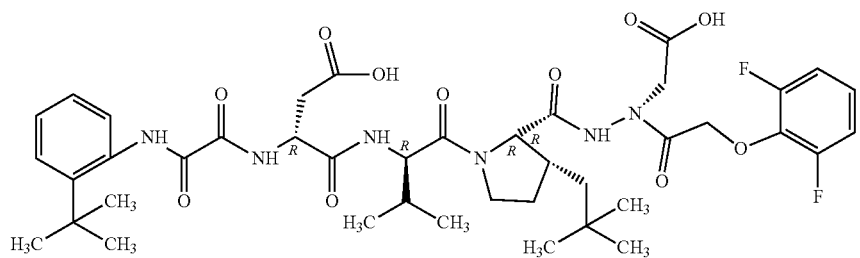
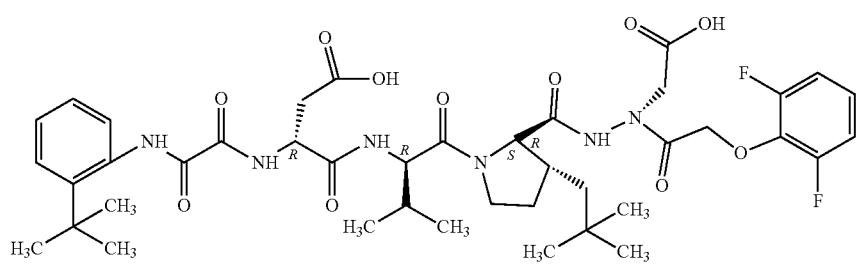

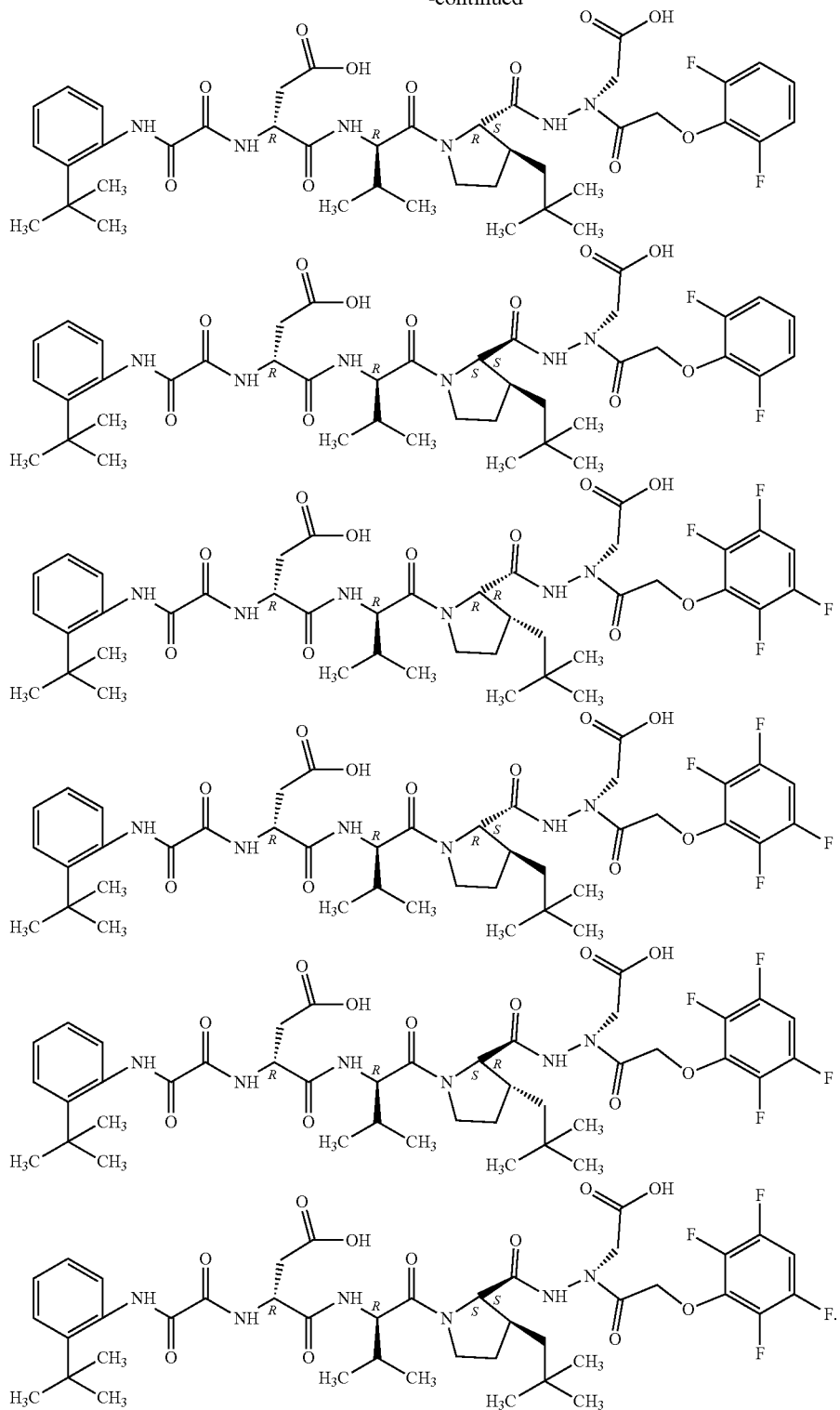
* * * * *